(12) United States Patent
Gurney et al.

(10) Patent No.: US 12,729,357 B2
(45) Date of Patent: Sep. 8, 2026

(54) MICROSCALE BIOREACTOR SYSTEM FOR AND METHOD OF PROVIDING CELL CULTURE GROWTH CONDITIONS IN A SMALL-VOLUME VESSEL

(71) Applicant: Redbud Labs, Inc., Research Triangle Park, NC (US)

(72) Inventors: Travis Gurney, Research Triangle Park, NC (US); Jay Kenneth Fisher, Research Triangle Park, NC (US); Brittany Mason, Research Triangle Park, NC (US); Richard Chasen Spero, Research Triangle Park, NC (US)

(73) Assignee: Redbud Labs, Inc., Research Triangle Park, NC (US)

( * ) Notice: Subject to any disclaimer, the term of this patent is extended or adjusted under 35 U.S.C. 154(b) by 615 days.

(21) Appl. No.: 18/014,967

(22) PCT Filed: Jul. 7, 2021

(86) PCT No.: PCT/US2021/040635

§ 371 (c)(1),
(2) Date: Jan. 6, 2023

(87) PCT Pub. No.: WO2022/010982

PCT Pub. Date: Jan. 13, 2022

(65) Prior Publication Data

US 2023/0257689 A1 Aug. 17, 2023

Related U.S. Application Data

(60) Provisional application No. 63/065,149, filed on Aug. 13, 2020, provisional application No. 63/048,779, filed on Jul. 7, 2020.

(51) Int. Cl.
*C12M 1/32* (2006.01)
*B01F 33/30* (2022.01)
(Continued)

(52) U.S. Cl.
CPC ......... *C12M 23/12* (2013.01); *B01F 33/3038* (2022.01); *C12M 27/02* (2013.01); *B01F 2101/44* (2022.01); *B01F 2215/0431* (2013.01)

(58) Field of Classification Search
CPC ...... C12M 23/12; C12M 27/02; C12M 41/34; B01F 33/3038; B01F 2101/44;
(Continued)

(56) References Cited

U.S. PATENT DOCUMENTS 9,238,869 B2 * 1/2016 Superfine .................. C23F 1/04
2004/0214315 A1 10/2004 Saluz et al.
(Continued)

FOREIGN PATENT DOCUMENTS

WO WO-2018236833 A1 * 12/2018 ........ B01L 3/502746

OTHER PUBLICATIONS

International Search Report and Written Opinion issued in counterpart PCT Application No. PCT/US2021/040635 dated Oct. 13, 2021 (ten (10) pages).

*Primary Examiner* — Michael L Hobbs
(74) *Attorney, Agent, or Firm* — E. Eric Mills; Nicholas P. Stadnyk; Maynard Nexsen PC

(57) ABSTRACT

A microscale bioreactor system for and method is disclosed for providing improved cell culture growth conditions in a small-volume vessel. For example, a microbioreactor system is provided that may include a small-volume vessel and wherein the small-volume vessel may include a field of actuatable surface-attached microposts. Further, the microbioreactor system may include an actuation mechanism for actuating the surface-attached microposts into movement. In
(Continued)

some embodiments, the surface-attached microposts may be functionalized with, for example, activation signals for converting standard T-cells in a growth media to activated T-cells. Further, a method of using the microbioreactor system for providing cell culture growth conditions including enhanced oxygenation and nutrients distribution in a small-volume vessel is provided.

14 Claims, 16 Drawing Sheets

(51) Int. Cl.
*C12M 1/06* (2006.01)
*B01F 101/44* (2022.01)

(58) Field of Classification Search
CPC ........ B01F 2215/0431; C12N 2529/00; C12N 2537/00; B01L 3/5085; B01L 3/502746; B01L 3/502761; B01L 2300/0829; B01L 2300/0851; B01L 2400/043
See application file for complete search history.

(56) References Cited

U.S. PATENT DOCUMENTS

2016/0209313 A1 7/2016 Superfine et al.
2019/0076840 A1 3/2019 Gottardi et al.
2019/0336971 A1 11/2019 Wikswo et al.

* cited by examiner 210
110
110
110
212
120
214
216
A-A

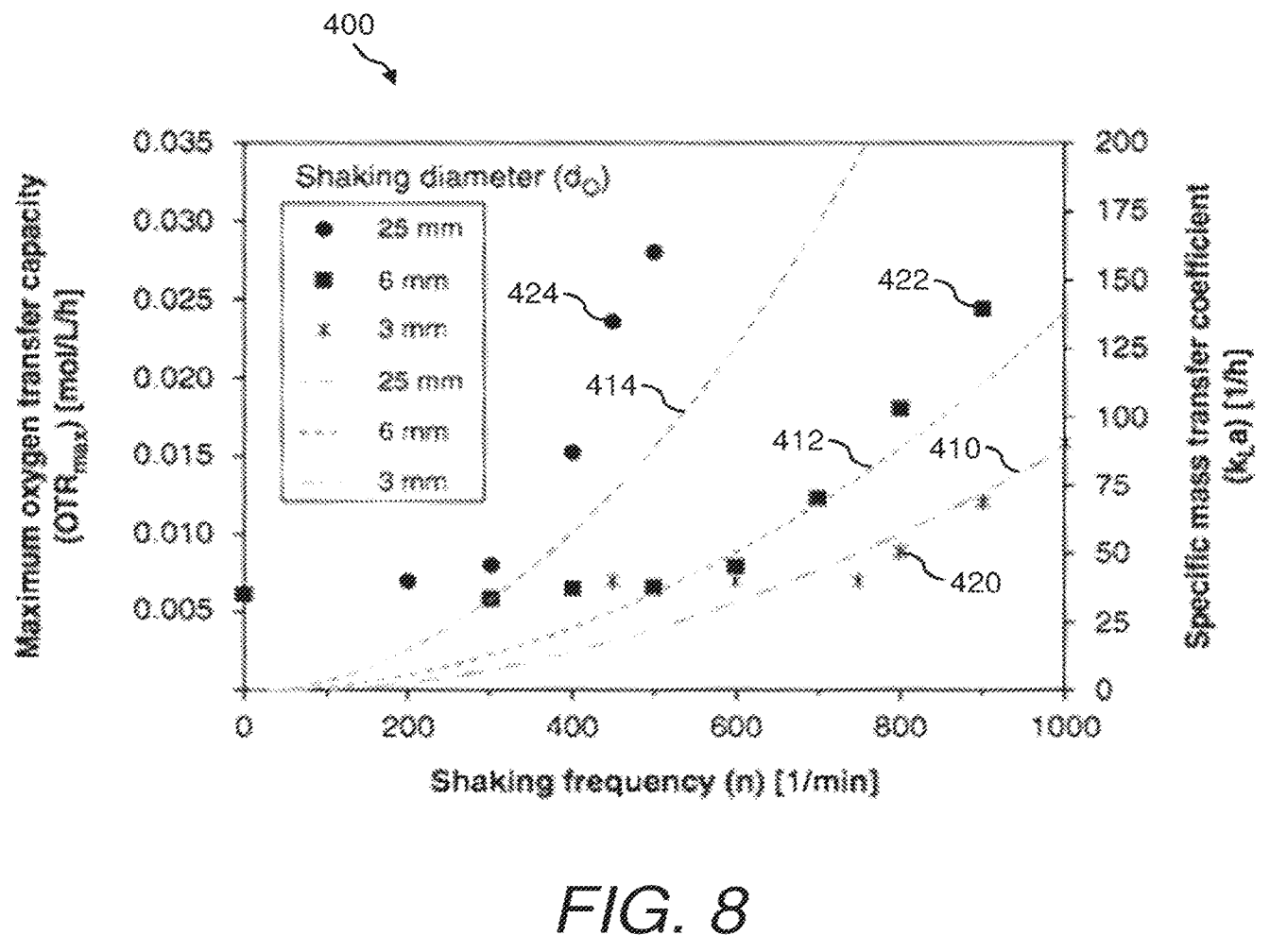

400

Specific mass transfer coefficient ($k_La$) [1/h]

200 175 150 125 100 75 50 25 0

Maximum oxygen transfer capacity ($OTR_{max}$) [mol/L/h]

0.035 0.030 0.025 0.020 0.015 0.010 0.005

Shaking diameter ($d_O$)

25 mm 6 mm 3 mm 25 mm 6 mm 3 mm 410 412 414 420 422 424

0 200 400 600 800 1000

Shaking frequency (n) [1/min]

FIG. 8

MICROSCALE BIOREACTOR SYSTEM FOR AND METHOD OF PROVIDING CELL CULTURE GROWTH CONDITIONS IN A SMALL-VOLUME VESSEL

CROSS REFERENCE TO RELATED APPLICATIONS

The presently disclosed subject matter is a 35 U.S.C. § 371 U.S. national phase entry of International Application No. PCT/US2021/040635 having an international filing date of Jul. 7, 2020, which is related to and claims priority to U.S. Provisional Patent Application No. 63/048,779, entitled "MICROSCALE BIOREACTOR SYSTEM FOR AND METHOD OF PROVIDING CELL CULTURE GROWTH CONDITIONS IN A SMALL-VOLUME VESSEL," filed on Jul. 7, 2020, and U.S. Provisional Patent Application No. 63/065,149, entitled MICROSCALE BIOREACTOR SYSTEM FOR AND METHOD OF PROVIDING CELL CULTURE GROWTH CONDITIONS IN A SMALL-VOLUME VESSEL," filed on Aug. 13, 2020; the entire disclosures of which are incorporated herein by reference.

FIELD OF THE INVENTION

The invention relates generally to the processing of biological materials and more particularly to a microscale bioreactor system for and method of providing cell culture growth conditions in a small-volume vessel.

BACKGROUND

Cell culture is a process for growing cells under controlled conditions outside their natural environment. After isolating cells of interest from their biological source, such as living tissue, they can be maintained under carefully controlled conditions. Conditions vary for each cell type, but generally consist of a suitable vessel with a substrate or medium that supplies the essential nutrients (amino acids, carbohydrates, vitamins, minerals), growth factors, hormones, and gases ($CO_2$, $O_2$), and regulates the physio-chemical environment (pH buffer, osmotic pressure, temperature). Most cells require a surface or an artificial substrate (adherent or monolayer culture) whereas others can be grown free floating in culture medium (suspension culture). The lifespan of cells is genetically determined, but some cells have been "transformed" into immortal cells that will reproduce indefinitely if the optimal conditions are provided.

Cell culture processes generally take place in bioreactor vessels or flasks ranging in capacity, for example, from about 100 mL to about 6000 mL (6 L). Currently, certain technology and/or processes exist for maintaining controlled growth conditions in these sized vessels. These culture vessels or flasks may be considered large-volume vessels compared with, for example, the capacity of the individual wells in multi-well microplates. The volumes of liquid required for cell culture processes and/or experiments in these large-volume vessels can be costly.

There is a need for cell culture processes and/or experiments in small-volume vessels or chambers, such as in multiwell microplates.

SUMMARY OF THE INVENTION

The invention provides a small-volume bioreactor. The small-volume bioreactor may include a small-volume well layer comprising an array of wells, each well having a top opening and a bottom opening. The small-volume bioreactor may include an active surface layer sealingly affixed to the array of wells thereby exposing an active surface to the interior of the wells of the array of wells via the bottom openings of the well layer. In some cases, the active surface layer comprises microposts.

The active surface layer may include microposts extending into the interior of the wells of the array of wells via the bottom openings of the well layer. An intermediate layer may be interposed between the well layer and the active surface layer, as well as a backing layer affixed to the active surface layer.

An active surface layer may be sealingly affixed to the well layer by a fixation means. For example, the fixation means may be an adhesive gasket situated between the active surface layer and the well layer; an adhesive situated between the active surface layer and the well layer; or a welding technique.

The small-volume bioreactor of the invention may include a cell culture in one or more of the wells of the array of wells.

In certain embodiments of the invention, each well has a size in the range of about 3 mm to about 100 mm in diameter, preferably in the range of about 6 mm to about 25 mm in diameter.

In certain embodiments of the invention, each well may have a volume in the range of from about 0.05 to about 100 mL, preferably in the range of from about 0.05 to about 10 mL.

In certain embodiments of the invention, the wells may be oriented in an x by z array, wherein x and z are each in the range of 2 wells to 1,000 wells.

The microposts of the invention may in certain embodiments be functionalized with molecules that interact with cells in the culture to produce a biological effect in the cells.

The micropost array may, in some embodiments, include a magnetically-responsive material. In some cases, the magnetically-responsive material is a paramagnetic material, a ferromagnetic material, a ferrimagnetic material, or a metamagnetic material.

In various embodiments, the small-volume bioreactor of the invention may be batch, fed-batch, or continuous.

The invention also provides an instrument including a means for mounting a small-volume bioreactor in operational proximity to a magnetic actuation mechanism. The instrument may also include the magnetic actuation mechanism. The small-volume bioreactor may be mounted on the means for mounting a small-volume bioreactor. The instrument may include a computing means electronically coupled to, and programmed to control, the magnetic actuation mechanism.

The invention also provides a method of cultivating cells. The method may include providing in one or more of the wells of a system of the invention cell culture media comprising cells. The method may include causing the instrument to circulate the cell culture media and cells via movement of the microposts controlled by the computing means. The cells may, for example, be prokaryotic cells and/or eukaryotic cells.

The invention also provides a method of maintaining cell culture growth conditions within a small-volume bioreactor. The method may include placing cell culture media in contact with a small-volume well layer comprising an array of wells, each well having a top opening and a bottom opening. The method may include placing the cell culture media in contact with an active surface having microposts affixed to the well layer such that the microposts extend into the bottom openings of the well layer. The method may include actuating the movement of the surface-attached microposts to create a mixing action whereby the mixing action maintains cell culture growth conditions within the small-volume bioreactor.

In certain embodiments of the invention, mixing efficiency of the surface-attached microposts is quantified by measuring an oxygen transfer coefficient (kLa) of the cell culture media.

The surface-attached microposts may, in some embodiments, include a magnetically-responsive material. In some cases, the magnetically-responsive material is a paramagnetic material, a ferromagnetic material, a ferrimagnetic material, or a metamagnetic material.

The surface-attached microposts of the invention may, in certain embodiments, be functionalized with molecules that interact with cells in the culture to produce a biological effect in the cells.

In certain embodiments, the microposts of the invention may be functionalized with molecules that convert standard T-cells in a growth media to activated T-cells.

The invention also provides a method of maintaining cell culture growth conditions within a small-volume bioreactor. The method may include placing cell culture media in wells of a small-volume well layer comprising an array of wells, each well having a top opening and a bottom opening. The method may include placing cell culture media in contact with an active surface layer. The method may include generating an actuation force in proximity to the active surface layer, thereby compelling the active surface layer to create a mixing action whereby the mixing action maintains cell culture growth conditions within the wells.

In certain embodiments of the invention, the active surface layer may include an array of actuatable surface-attached microposts.

In certain embodiments of the invention, the generation of the actuation force in proximity to the array of actuatable surface-attached microposts compels the microposts to create a mixing action, whereby the mixing action maintains cell culture growth conditions within the wells.

In certain embodiments of the invention, mixing efficiency of the actuatable surface-attached microposts is quantified by measuring an oxygen transfer coefficient (kLa) of the cell culture media.

The actuatable surface-attached microposts may, in some embodiments, include a magnetically-responsive material. In some cases, the magnetically-responsive material is a paramagnetic material, a ferromagnetic material, a ferrimagnetic material, or a metamagnetic material.

The actuatable surface-attached microposts of the invention may, in certain embodiments, be functionalized with molecules that interact with cells in the culture to produce a biological effect in the cells.

The microposts of the invention may, in certain embodiments, be functionalized with molecules that convert standard T-cells in a growth media to activated T-cells.

BRIEF DESCRIPTION OF THE DRAWINGS

The accompanying drawings, which are incorporated in and constitute a part of this specification, illustrate certain embodiments, and together with the written description, serve to explain certain principles of the methods, devices and systems disclosed herein. The drawings are included by way of example and not by way of limitation. Like reference numerals identify like components throughout the drawings, unless the context indicates otherwise. Some or all of the figures may be schematic representations.

FIG. 8 shows a plot indicating the mixing efficiency of traditional small-volume culture wells in response to varying orbital shaking frequency.

DEFINITIONS

Figure 1:
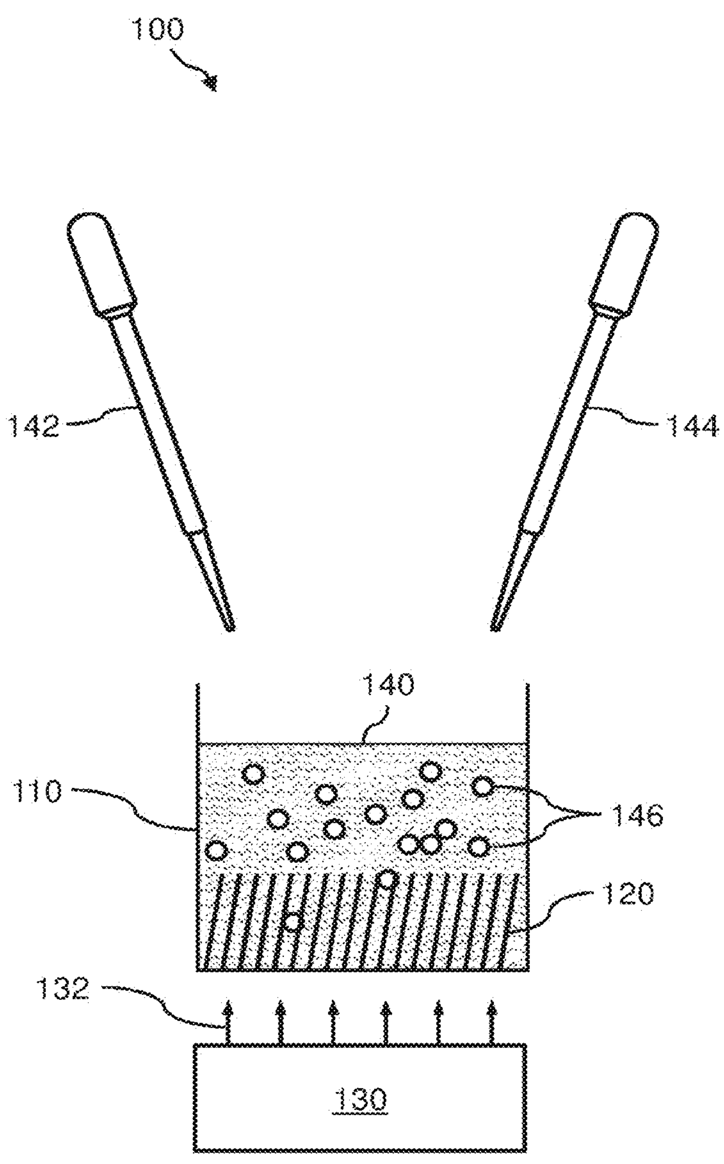
FIG. 1 is a schematic diagram of an example of the microbioreactor system for providing cell culture growth conditions including enhanced oxygenation and nutrients distribution in small-volume vessels.

“Active surface” means any surface that has properties or components for manipulating liquid in a small volume well. Manipulation can include, for example, flowing the liquid, circulating liquid, fractionating the liquid, and/or establishing or eliminating concentration gradients within the liquid. Examples of suitable surface properties include projections such as posts, especially projections that may be caused to move by an external force. Examples of suitable surface properties also include texture or topography of the surface; physical perturbation of the surface by vibration or deformation, electrical, electronic, electromagnetic, and/or magnetic forces; and optically-active surfaces (e.g., lenses) that interact with external light sources. Additional examples of active surfaces are provided in International Patent Publication No. WO2018236833A1, entitled "Modular active surface devices for microfluidic systems and methods of making same," published on 27 Dec. 2018, the entire disclosure of which is incorporated herein by reference.

"Sample" means a source of cells for culturing. Examples of samples include biological materials, fluids, environmental samples (e.g., water samples, air samples, soil samples, solid and liquid wastes, and animal and vegetable tissues), and industrial samples (e.g., food, reagents, and the like).

"Manipulation," with respect to a sample, means causing a physical change in a cell sample or culture. Examples of manipulation include generating fluid flow, altering the flow profile of an externally driven fluid, fractionating the sample into constituent parts, establishing or eliminating concentration gradients, and the like. Examples of surface properties useful for manipulation include post technology—whether static or actuated (i.e., activated). The surface properties may also include microscale texture or topography in the surface, physical perturbation of the surface by vibration or deformation; electrical, electronic, electromagnetic, and/or magnetic system on or in the surface; optically active (e.g., lenses) surfaces, such as embedded light-emitting diodes (LEDs) or materials that interact with external light sources; and the like.

"Small volume" means the typical volumes used to culture cells in standard growth plates, e.g., from about 0.05 to about 10 mL per well.

"Surface-attached post" or "surface-attached micropost" or "surface-attached structure" or "micropost" are used interchangeably. Generally, a surface-attached structure has two opposing ends: a fixed end and a free end. The fixed end may be attached to a substrate by any suitable means, depending on the fabrication technique and materials employed. The fixed end may be "attached" by being integrally formed with or adjoined to the substrate, such as by a microfabrication process. Alternatively, the fixed end may be "attached" via a bonding, adhesion, fusion, or welding process. The surface-attached structure has a length defined from the fixed end to the free end, and a cross-section lying in a plane orthogonal to the length. For example, using the Cartesian coordinate system as a frame of reference, and associating the length of the surface-attached structure with the z-axis (which may be a curved axis), the cross-section of the surface-attached structure lies in the x-y plane.

The cross-section of the surface-attached structure may have any shape, such as rounded (e.g., circular, elliptical, etc.), polygonal (or prismatic, rectilinear, etc.), polygonal with rounded features (e.g., rectilinear with rounded corners), or irregular. The cross-section may be symmetrical or asymmetrical. The size of the cross-section of the surface-attached structure in the x-y plane may be defined by the "characteristic dimension" of the cross-section, which is shape-dependent. As examples, the characteristic dimension may be diameter in the case of a circular cross-section, major axis in the case of an elliptical cross-section, or maximum length or width in the case of a polygonal cross-section. The characteristic dimension of an irregularly shaped cross-section may be estimated as the dimension characteristic of a regularly shaped cross-section that the irregularly shaped cross-section most closely approximates (e.g., the diameter of a circle, major axis of an ellipse, length or width of a polygon, etc.).

A surface-attached structure as described herein may be non-movable (static, rigid, etc.) or movable (flexible, deflectable, bendable, etc.) relative to its fixed end or point of attachment to the substrate. To facilitate the movability of movable surface-attached structures, the surface-attached structure may include a flexible body composed of an elastomeric (flexible) material, and may have an elongated geometry in the sense that the dominant dimension of the surface-attached structure is its length—that is, the length is substantially greater than the characteristic dimension. Examples of the composition of the flexible body include, but are not limited to, elastomeric materials such as hydrogel and other active surface materials (for example, polydimethylsiloxane (PDMS)).

The movable surface-attached structure may be configured such that the movement of the surface-attached structure relative to its fixed end may be actuated or induced in a non-contacting manner by an actuation force. For example, to render the surface-attached structure movable by an applied magnetic or electric field, the surface-attached structure may include an appropriate metallic component disposed on or in the flexible body of the surface-attached structure. To render the surface-attached structure responsive to a magnetic field, the metallic component may be a ferromagnetic material such as, for example, iron, nickel, cobalt, or magnetic alloys thereof, one non-limiting example being "alnico" (an iron alloy containing aluminum, nickel, and cobalt). To render the surface-attached structure responsive to an electric field, the metallic component may be a metal exhibiting electrical conductivity such as, for example, copper, aluminum, gold, and silver, and various other metals and metal alloys. Depending on the fabrication technique utilized, the metallic component may be formed as a layer (or coating, film, etc.) on the outside surface of the flexible body at a selected region of the flexible body along its length. The layer may be a continuous layer or a densely grouped arrangement of particles. Alternatively, the metallic component may be formed as an arrangement of particles embedded in the flexible body at a selected region thereof.

"Actuation force" means the force applied to the microposts. For example, the actuation force may include a magnetic, thermal, sonic, or electric force. Notably, the actuation force may be applied as a function of frequency or amplitude, or as an impulse force (i.e., a step function). Similarly, other actuation forces may be used without departing from the scope of the present subject matter, such as fluid flow across the micropost array (e.g., flexible microposts that are used as flow sensors via monitoring their tilt angle with an optical system). In one example, the actuation force is an applied magnetic or electric field of a desired strength, field line orientation, and frequency (which may be zero in the case of a magnetostatic or electrostatic field).

Application of an actuation force actuates the movable surface-attached microposts into movement. For example, the actuation may occur by contacting the cell processing chamber with a control instrument comprising elements that provide an actuation force, such as a magnetic or electric field. Accordingly, the control instrument includes, for example, any mechanisms for actuating the microposts (e.g., magnetic system), any mechanisms for counting the cells (e.g., imaging system), the pneumatics for pumping the fluids (e.g., pumps, fluid ports, valves), and a controller (e.g., microprocessor).

"Flow cell" means any chamber comprising a solid surface across which one or more liquids can be flowed, wherein the chamber has at least one inlet and at least one outlet. The surface-attached microposts may be arranged to project into a flow cell and may include a size and quantity of microposts sufficient to manipulate contents of the flow cell.

"Micropost array" means an array of small posts, extending outwards from a substrate, that typically range from 1 to 100 micrometers in height. In one embodiment, microposts of a micropost array may be vertically-aligned. Notably, each micropost includes a proximal end that is attached to the substrate base and a distal end or tip that is opposite the proximal end. Microposts may be arranged in arrays such as, for example, the microposts described in U.S. Pat. No. 9,238,869, entitled "Methods and systems for using actuated surface-attached posts for assessing biofluid rheology," issued on Jan. 19, 2016; the entire disclosure of which is incorporated herein by reference. U.S. Pat. No. 9,238,869 describes methods, systems, and computer readable media for using actuated surface-attached posts for assessing biofluid rheology. One method described in U.S. Pat. No. 9,238,869 is directed to testing properties of a biofluid specimen that includes placing the specimen onto a micropost array having a plurality of microposts extending outwards from a substrate, wherein each micropost includes a proximal end attached to the substrate and a distal end opposite the proximal end, and generating an actuation force in proximity to the micropost array to actuate the microposts, thereby compelling at least some of the microposts to exhibit motion. This method includes measuring the motion of at least one of the microposts in response to the actuation force and determining a property of the specimen based on the measured motion of the at least one micropost.

U.S. Pat. No. 9,238,869 also states that the microposts and micropost substrate of the micropost array can be formed of polydimethylsiloxane (PDMS). Further, microposts may include a flexible body and a metallic component disposed on or in the body, wherein application of a magnetic or electric field actuates the microposts into movement relative to the surface to which they are attached (e.g., wherein the actuation force generated by the actuation mechanism is a magnetic and/or electrical actuation force).

"Magnetically responsive" means responsive to a magnetic field. "Magnetically responsive microposts" include or are composed of magnetically responsive materials. Examples of magnetically responsive materials include, but are not limited to, paramagnetic materials, ferromagnetic materials, ferrimagnetic materials, and metamagnetic materials. Examples of suitable paramagnetic materials include iron, nickel, and cobalt, as well as metal oxides, such as, but not limited to, ferroferric oxide ($Fe_3O_4$), barium hexaferrite ($BaFe_{12}O_{19}$), cobalt(II) oxide (CoO), nickel(II) oxide (NiO), manganese(III) oxide ($Mn_2O_3$), chromium(III) oxide ($Cr_2O_3$), and cobalt manganese phosphide (CoMnP).

"Micropost field" or "micropost array" means a field or an array of small posts, extending outwards from a substrate. The posts typically range from about 1 to about 100 micrometers in height.

The terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Numbers expressing amounts, sizes, dimensions, proportions, shapes, formulations, parameters, percentages, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the invention. The term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

DETAILED DESCRIPTION

The invention will now be described more fully with reference to the accompanying drawings, in which some, but not all embodiments of the invention are shown. Like numbers refer to like elements throughout. The invention may be embodied in many different forms and should not be construed as limited to the embodiments set forth herein; rather, these embodiments are provided so that this disclosure will satisfy applicable legal requirements. In view of the instant disclosure, many modifications and other embodiments of the invention set forth herein will be apparent to one skilled in the art to which the invention pertains. The invention is not to be limited to the specific embodiments disclosed and that modifications and other embodiments are intended to be included within the scope of the appended claims.

Microscale Bioreactor

In some embodiments, the invention provides a microscale bioreactor system for and method of providing cell culture growth conditions in a small-volume vessel. For example, the invention provides a small-volume bioreactor system (that can also be referred to as a "microbioreactor" system). The bioreactor system may include a small-volume vessel. The small-volume vessel may include a field of actuatable surface-attached microposts. The microbioreactor system may include an actuation mechanism for actuating the surface-attached microposts into movement relative to the surface to which they are attached. The microposts may provide mixing action in any vessel and/or chamber in which they are installed.

In some embodiments, the invention provides a magnetic-based actuation mechanism for actuating magnetically responsive surface-attached microposts into movement relative to the surface to which they are attached and thereby provide mixing action in any vessel and/or chamber in which they are installed.

In some embodiments, the invention provides a field of actuatable surface-attached microposts for maintaining cell culture growth conditions in a small-volume vessel, such as but not limited to, a small-volume flask (e.g., 125 mL shake flask) and/or the individual wells of a standard size multi-well microplate (e.g., standard size 96-well, 48-well, 24-well, 16-well, 12-well, 8-well, 6-well, 4-well microplates, etc.). For example, the well-volume capacity of a standard size 96-well microplate may be about 300 μL, the well-volume capacity of a standard size 6-well microplate may be about 1-2 mL, and so on. These well-volume capacities are as compared with standard large-scale bioreactors that may be processing up to, for example, about 6 liters of liquid in a large-volume vessel.

In some embodiments, the invention provides a field of actuatable surface-attached microposts for maintaining cell culture growth conditions including, but not limited to, oxygenation and nutrients distribution (or homogenization) in a small-volume vessel.

In some embodiments, the invention provides a field of actuatable surface-attached microposts for maintaining cell culture growth conditions in a small-volume vessel by the mixing action of the microposts and wherein the mixing efficiency of the microposts may be quantified by measuring the oxygen transfer coefficient (kLa) of the cell culture media.

In some embodiments, the invention provides a field of actuatable surface-attached microposts for maintaining cell culture growth conditions in a small-volume vessel and the surface-attached microposts are functionalized with molecules that interact with cells in the culture to produce a biological effect in the cells. For example, the posts may be functionalized with a ligand for cell-surface receptors, the cell surface, or the cell membrane, of some or all of the cells in the culture. In operation, when cells in the culture contact the ligand, they may interact with the ligand via the cell surface receptors or the cell surface. The interaction may, for example, include the cells binding to the posts, activation of a biological process in the cells as a result of the interaction between the ligand and the cell or cell's receptor.

In some embodiments, the microbioreactor system and method utilize functionalized microposts, not functionalized beads, to interact with cells in small-volume vessels and wherein the interaction produces a biological response.

In some embodiments, the microbioreactor system and method utilize functionalized microposts together with functionalized beads to interact with cells in small-volume vessels and wherein the interaction produces a biological response. For example, the posts may be functionalized with activation signals for standard T-cells. T cells cultured in the presence of the functionalized posts may be converted into activated T-cells. The mixing action of the surface-attached microposts enhances contact between the functionalized microposts and the standard T-cells to be converted into activated T-cells.

In some embodiments, the invention makes use of functionalized microposts, not functionalized beads, to activate T-cells in small-volume vessels and wherein the activated T-cells may be produced in a manner that can be counted accurately because beads that can be mistakenly counted as cells are not present.

In some embodiments, the operation of the microbioreactor system and method may be classified as batch, fed-batch, and/or continuous.

In some embodiments, the invention provides a low-cost alternative for performing cell culture as compared with standard large-scale bioreactors.

In some embodiments, the invention provides a wafer-level microbioreactor structure that includes a manifold portion that supports a small-volume vessels portion and wherein the wafer-level microbioreactor structure is designed for the mass production and/or operation of small-volume vessels in a cell culture application.

FIG. 1 is a schematic diagram of an example of the microbioreactor system 100 (i.e., a small-volume bioreactor). Microbioreactor system 100 is useful for providing cell culture growth conditions including enhanced oxygenation and nutrients distribution (or homogenization) in a small-volume vessel. Microbioreactor system 100 may include, for example, a small-volume vessel 110 that has a field of microposts 120 arranged on at least one surface therein. In microbioreactor system 100, "small-volume vessel" means the (smaller) well-volume capacity as compared with the capacity of the vessels used in standard large-scale bioreactors, which may be, for example, up to about 6 liters. Accordingly, the well-volume capacity of small-volume vessel 110 may be, for example, from about a few microliters (μL) to about a few milliliters (mL). In microbioreactor system 100, the top of small-volume vessel 110 may be open or closed.

Microposts 120 may be, for example, magnetically-responsive, actuatable, surface-attached microposts. Accordingly, microbioreactor system 100 may include an actuation mechanism 130 arranged in close proximity to small-volume vessel 110 that has the field of microposts 120. Actuation mechanism 130 may be any mechanism for actuating microposts 120 of small-volume vessel 110 in microbioreactor system 100. As used herein, the term "actuation force" refers to the force applied to microposts 120. Actuation mechanism 130 is used to generate an actuation force in proximity to microposts 120 that compels at least some of microposts 120 to exhibit motion. The actuation force may be, for example, magnetic, thermal, sonic, and/or electric force. The actuation force may be applied as a function of frequency or amplitude, or as an impulse force (i.e., a step function). Similarly, other actuation forces may be used without departing from the scope of the present subject matter, such as fluid flow across the field of microposts 120. In one example, microposts 120 are magnetically responsive microposts and actuation mechanism 130 may be one of the magnetic-based actuation mechanisms described with reference to U.S. patent application Ser. No. 62/654,048, entitled "Magnetic-Based Actuation Mechanisms for and Methods of Actuating Magnetically Responsive Microposts in a Reaction Chamber," filed on Apr. 16, 2018; the entire disclosure of which is incorporated herein by reference.

By actuating microposts 120 and causing motion thereof, any fluid (e.g., growth media 140) in small-volume vessel 110 is in effect stirred or caused to flow or circulate within small-volume vessel 110. Additionally, FIG. 1 shows cells 146 suspended in growth media 140 in small-volume vessel 110. Cells 146 may be, for example, any cells to be replicated in a cell culture process. Cells 146 may be, for example, T-cells or Chinese hamster ovary (CHO) cells. In another example, the cells 146 to be processed in growth media may adhere to surfaces of the microbioreactor, including for example the posts (see FIG. 13). Accordingly, microbioreactor system 100 may be useful for growing cells in a suspension cell culture configuration and/or an adherent cell culture configuration.

The field of microposts 120 may be based on, for example, the microposts described in the U.S. Pat. No. 9,238,869, entitled "Methods and systems for using actuated surface-attached posts for assessing biofluid rheology," issued on Jan. 19, 2016; the entire disclosure of which is incorporated herein by reference. The '869 patent describes methods, systems, and computer readable media for using actuated surface-attached posts for assessing biofluid rheology. According to one aspect, a method of the '869 patent for testing properties of a biofluid specimen includes placing the specimen onto a micropost array having a plurality of microposts extending outwards from a substrate, wherein each micropost includes a proximal end attached to the substrate and a distal end opposite the proximal end, and generating an actuation force in proximity to the micropost array to actuate the microposts, thereby compelling at least some of the microposts to exhibit motion. The method of the '869 patent includes measuring the motion of at least one of the microposts in response to the actuation force and determining a property of the specimen based on the measured motion of at least one micropost.

In one example, microposts 120 may be formed of polydimethylsiloxane (PDMS). Microposts 120 may include a flexible body and a metallic component disposed on or in the body, wherein application of a magnetic or electric field actuates microposts 120 into movement relative to the surface to which they are attached. In this example, the actuation force 132 generated by actuation mechanism 130 is a magnetic and/or electrical actuation force. More details of microposts 120 are shown and described below with reference to FIG. 2A through FIG. 3B.

Referring still to FIG. 1, in microbioreactor system 100, various fluidic operations, such as, but not limited to, mixing operations, washing operations, binding operations, and cell processing operations, may take place within small-volume vessel 110. In one example, cell culture operations take place within small-volume vessel 110. A liquid delivery mechanism 142 and a liquid removal mechanism 144 may be provided with respect to small-volume vessel 110. In one example, liquid delivery mechanism 142 and liquid removal mechanism 144 may be pipettes, which may in some cases be robotically operated. The operation of microbioreactor system 100 may, without limitation, be classified as batch, fed-batch, and/or continuous.

In microbioreactor system 100, microposts 120 may provide the following functions (among others): (1) provide mixing action to enhance oxygenation levels in small-volume vessel 110, (2) provide mixing action to enhance nutrients distribution in small-volume vessel 110, and (3) provide a source of ligands for interacting with cultured cells, such as a source of activation signals for converting standard T-cells to activated T-cells. For example, microposts 120 may be used to facilitate, for example, more rapid mixing action within the vessel as compared to a vessel that is absent microposts 120. For example, in a cell culture application, the rapid mixing action of microposts 120 may be used to ensure that the oxygenation level and nutrients distribution is adequate to maintain desired cell culture growth conditions in small-volume vessel 110. More details of an example of experiments indicating oxygenation levels in a small-volume vessel due to certain mixing action are shown and described below with reference to FIG. 7A, FIG. 7B, FIG. 8, FIG. 9, and FIG. 10.

Additionally, in microbioreactor system 100, microposts 120 may be functionalized with, for example, activation signals for coming into contact with standard T-cells in a growth media 140 in small-volume vessel 110 and then converting them to activated T-cells. The mixing action of the surface-attached microposts 120 enhances contact between the functionalized microposts 120 and the standard T-cells to be converted into activated T-cells. More details of an example of microposts 120 functionalized with activation signals are shown and described below with reference to FIG. 11.

Figures 2A, 2B:
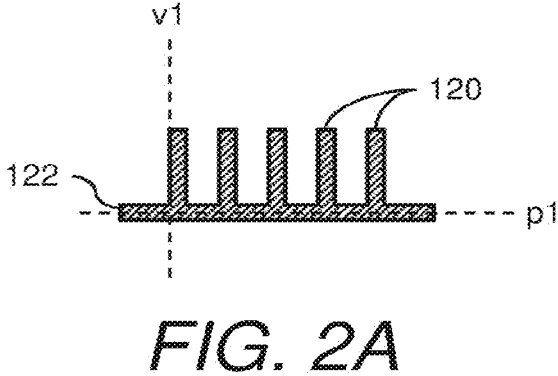
FIG. 2A and FIG. 2B illustrate side views of an example of microposts of the microbioreactor system.

FIG. 2A and FIG. 2B illustrate side views of microposts 120 arranged in a micropost field or array. In one embodiment, microposts of a micropost field or array are substantially vertical along a line v1 relative to a plane p1 established by substrate 122. Notably, each micropost includes a proximal end that is attached to substrate 122 and a distal end or tip that is opposite the proximal end. Accordingly, at least one surface of small-volume vessel 110 of microbioreactor system 100 may include an arrangement of microposts 120 on a substrate 122.

Figure 4:
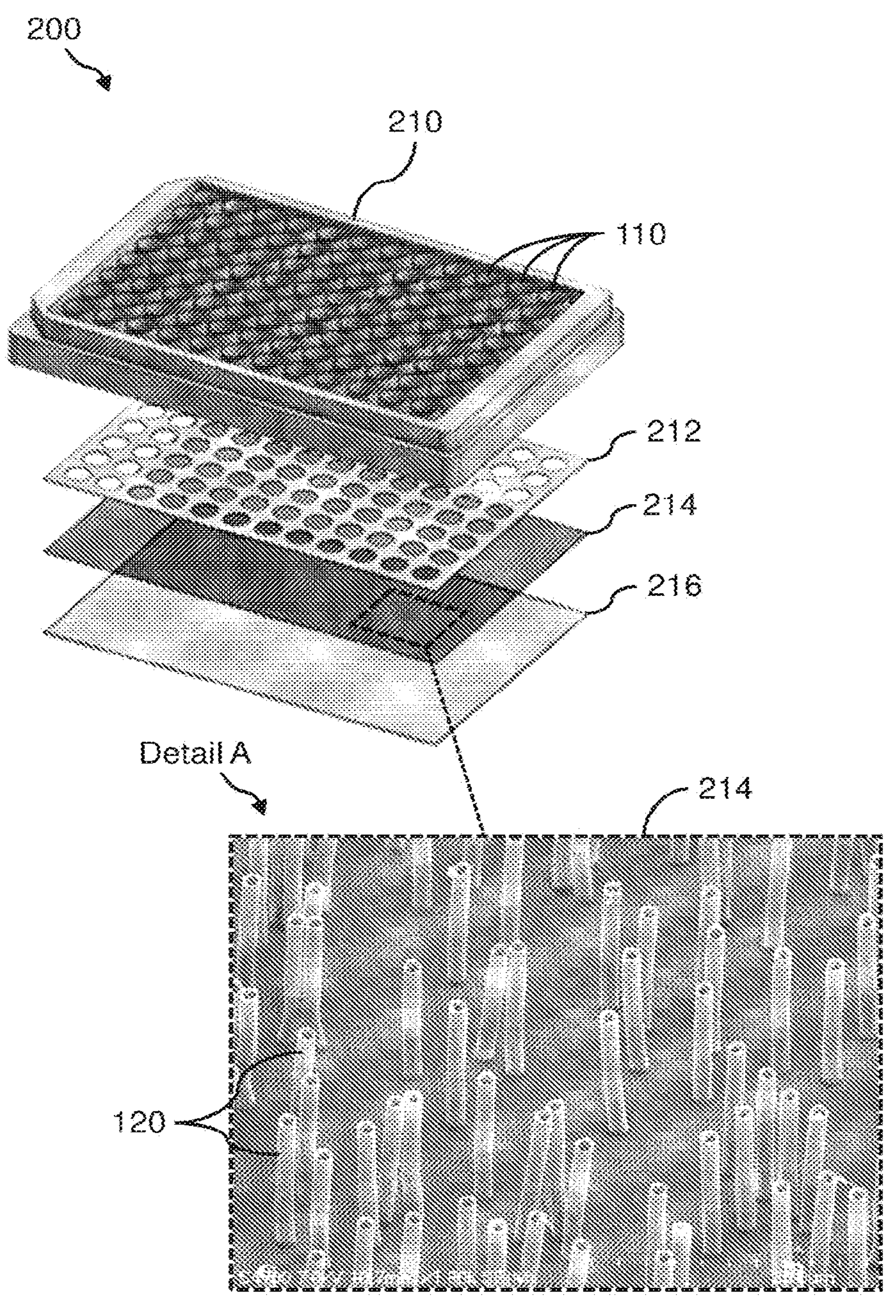
FIG. 4 illustrates an exploded view of an example of a small-volume well platform for use in the microbioreactor system.

Microposts 120 and substrate 122 can be formed, for example, of PDMS. The length, diameter, geometry, orientation, and pitch of microposts 120 in the field or array can vary. For example, the length of microposts 120 can vary from about 1 μm to about 100 μm. The diameter of microposts 120 can vary from about 0.1 μm to about 10 μm. The cross-sectional shape of microposts 120 can vary. For example, the cross-sectional shape of microposts 120 can be circular, ovular, square, rectangular, triangular, and so on. The orientation of microposts 120 can vary. For example, FIG. 2A shows microposts 120 having an axis along line v1 that is oriented substantially normal to the plane p1 of substrate 122, while FIG. 2B shows microposts 120 oriented at a tilt angle $\alpha$ with respect to the normal of the plane p1 of substrate 122. In a neutral position with no actuation force applied, the tilt angle $\alpha$ can be, for example, from about 0 degrees to about 45 degrees. Additionally, the pitch of microposts 120 within a micropost field or array can vary, for example, from about 0 μm to about 50 μm. The relative positions of microposts 120 within the micropost field or array can vary, and the microposts can have a regular or irregular pitch, as illustrated in FIG. 4. Where the pitch of microposts 120 within a micropost field or array is irregular, the pitch within the irregular array can vary for example, from about 0 μm to about 50 μm.

Figure 3A:
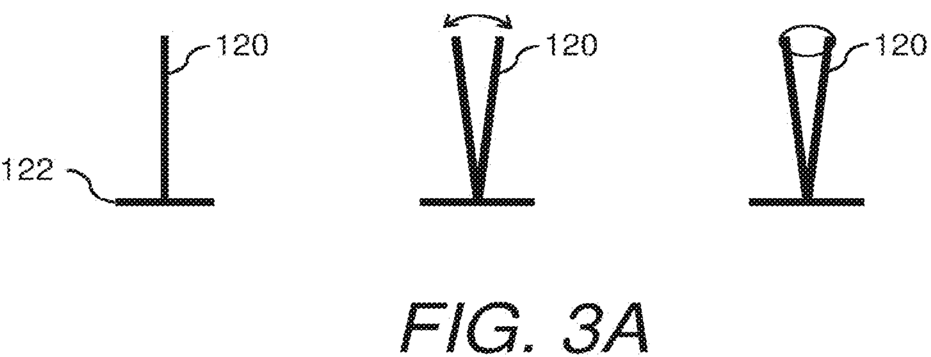
FIG. 3A and FIG. 3B illustrate side views of a micropost and show examples of the actuation motion thereof.
Figure 3B:
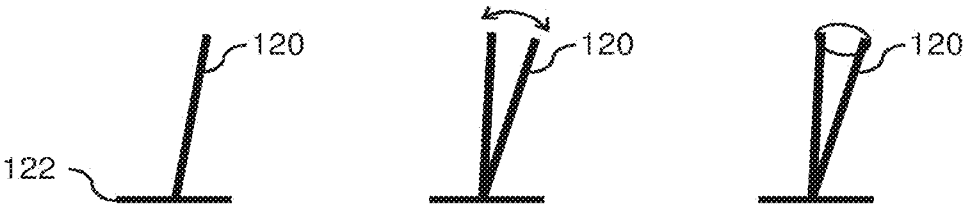

FIG. 3A and FIG. 3B is side views of a micropost 120 and show examples of the actuation motion thereof. For example, FIG. 3A shows an example of a micropost 120 oriented substantially normal to the plane of substrate 122 (see FIG. 2A). FIG. 3A shows that the distal end of the micropost 120 can move (1) with side-to-side 2D motion only with respect to the fixed proximal end or (2) with circular (or conical) motion with respect to the fixed proximal end, which is a cone-shaped motion. By contrast, FIG. 3B shows an example of a micropost 120 oriented at an angle with respect to the plane of substrate 122 (see FIG. 2B). FIG. 3B shows that the distal end of the micropost 120 can move (1) with tilted side-to-side 2D motion only with respect to the fixed proximal end or (2) with tilted circular motion with respect to the fixed proximal end, which is a tilted cone-shaped motion (or tilted conical motion). In microbioreactor system 100 and/or a small-volume well platform 200 (see FIG. 4), by actuating microposts 120 and causing motion thereof, any fluid in a certain small-volume vessel 110 is in effect stirred or caused to flow or circulate within the small-volume vessel 110 and across the surface area thereof. The cone-shaped motion of micropost 120 shown in FIG. 3A, as well as the tilted cone-shaped motion of micropost 120 shown in FIG. 3B, can be achieved using a rotating magnetic field. A rotating magnetic field is one example of actuation force 132 of magnetic actuation mechanism 130 of microbioreactor system 100. Magnetic actuation mechanism 130 may be configured to actuate the magnetically responsive surface-attached microposts 120 in certain beat patterns, such as synchronized beat patterns and/or metachronal beat patterns. Microposts 120 may be actuated in a manner to direct or force cells to a specific location inside a small-volume vessel 110 for any purpose.

Referring still to FIG. 1 through FIG. 3B, microposts 120 may be based on, for example, the microposts described in the '869 patent as described hereinabove. In one example, according to the '869 patent, microposts 120 and substrate 122 can be formed of PDMS. Microposts 120 may include a flexible body and a metallic component disposed on or in the body, wherein application of a magnetic or electric field actuates microposts 120 into movement relative to the surface to which they are attached. Again, in microbioreactor system 100, actuation force 132 generated by magnetic actuation mechanism 130 may be a magnetic actuation force. Accordingly, the magnetically responsive surface-attached microposts 120 in small-volume vessel 110 are positioned within the magnetic actuation force 132 generated by magnetic actuation mechanism 130.

To support the desired cell culture growth conditions, standard large-scale bioreactors used for cell culture may provide (1) a way to add, for example, reagents, nutrients, oxygen (i.e., the cell growth media) to the chamber or vessel; (2) mixing via, for example, an impeller or stir bars at the bottom of the vessel; (3) agitation or shaking via, for example, the vessel sitting on a rocker device; (4) aeration via, for example, a bubbler device; and so on. However, these mechanisms used in standard large-scale bioreactors may not be practical or applicable for use in cell culture small-volume vessels.

Accordingly, an important main benefit of the microbioreactor system 100 and method is that it may be used to replicate the cell culture growth conditions of standard large-scale bioreactors in a microscale cell culture environment. For example, microbioreactor system 100 may (1) provide liquid delivery mechanism 142 and liquid removal mechanism 144 (e.g., manual and/or automated pipetting) and/or microfluidics methods to supply, for example, reagents, nutrients, oxygen (i.e., the cell growth media) to small-volume vessel 110; (2) provide mixing via the magnetically responsive surface-attached microposts 120 in small-volume vessel 110; (3) mimic agitation or shaking via the magnetically responsive surface-attached microposts 120 in small-volume vessel 110; (4) provide aeration via the mixing action of the magnetically responsive surface-attached microposts 120 in an open-top small-volume vessel 110; and so on.

While microbioreactor system 100 shown in FIG. 1 shows a single small-volume vessel (i.e., a small-volume well or a small-volume bioreactor) 110, in other embodiments, microbioreactor system 100 may support multiple small-volume vessels 110 and with each including actuatable surface-attached microposts 120. By way of example, FIG. 4 shows an exploded view of an example of a small-volume well platform (i.e., a small-volume vessel platform or a small-volume bioreactor platform) 200 for use in the microbioreactor system 100. Small-volume well platform 200 may include one or multiple small-volume vessels 110 and may be arranged in close proximity to a magnetic actuation mechanism 130, as shown, for example, in FIG. 6.

In one example, small-volume well platform 200 may be based on any standard multi-well microplate. Generally, microplates are sealable multi-well plates that are used for a variety of applications, including assays, cell culture, sample storage, nucleic acid or protein quantification, and sample filtration. Typically made of plastic or glass, microplates are available in multiple formats, including 1536-well, 384-well, 96-well, 48-well, 24-well, 16-well, 12-well, 8-well, 6-well, 4-well microplates, and strips of wells that fit into plate frames. Different well-volume capacities, well shapes, plate colors, and plate coatings are available.

In one example, small-volume well platform 200 may be based on any standard multi-well cell culture microplate. Generally, multi-well cell culture microplates are designed to support the growth, attachment, and differentiation of cells, whether for ongoing culture or temporarily before cell-based assays; includes plates with sterile untreated surfaces or treated and/or coated surfaces. Examples include the Corning™ Costar™ Clear Polystyrene 96-Well Microplates, Corning™ 96-Well Clear Bottom Black or White Polystyrene Microplates, Falcon™ Polystyrene Microplates, Corning™ Costar™ Flat Bottom Cell Culture Plates, Gibco™ Collagen I, Coated Plate, 96 well, Thermo Scientific™ Nunc™ 96-Well Polystyrene Round Bottom Microwell Plates, Corning™ CellBIND™ 96-well Clear Flat Bottom Sterile Polystyrene Microplate with Lid, Greiner Bio-One CELLCOAT™ 96 Well Polystyrene Poly-D-Lysine Flat Bottom Cell Culture Microplate with Lid, Black, Greiner Bio-One CELLSTAR™ 384 Well Polystyrene Cell Culture Microplates, Fisherbrand™ Surface Treated SterileTissue Culture Plates, and Corning™ UV-Transparent Microplates, all available from Fisher Scientific, Waltham, Massachusetts.

The overall footprint of a standard multi-well microplate is substantially the same regardless of the number of wells. Accordingly, the larger the number of wells, the smaller the well-volume capacity. For example, the well-volume capacity of a standard 96-well microplate may be about 300 μL, while the well-volume capacity of a standard 6-well microplate may be about 1-2 mL, and so on. The example small-volume well platform 200 shown in FIG. 4 is based on a standard 96-well microplate. Accordingly, the small-volume well platform 200 shown in FIG. 4 includes 96 small-volume vessels 110 (i.e., small-volume wells) with each having a well-volume capacity of about 300 μL. However, this is exemplary only. Small-volume well platform 200 may include any number of small-volume vessels 110, such as, but not limited to, 1536, 384, 96, 48, 24, 16, 12, 8, 6, or 4 small-volume vessels 110.

Referring still to FIG. 4, small-volume well platform 200 may include an open bottom small-volume well layer 210 (e.g., a multi-well microplate) that includes, for example, the 96 small-volume vessels 110; a well mask layer 212; a microposts layer 214; and a backing layer 216. For example, open bottom multi-well microplate 210 may be substantially the same as a standard 96-well microplate except that the floor of the wells is absent; meaning the wells of open bottom multi-well microplate 210 are essentially open channels. Open bottom multi-well microplate 210 may be formed, for example, of plastic or glass. Then, the floor of small-volume well platform 200 is formed by the arrangement of well mask layer 212, microposts layer 214, and backing layer 216.

Well mask layer 212 may be, for example, a biocompatible adhesive or silicone gasket layer with openings that substantially correspond to the size and positions of the 96 small-volume vessels 110 in open bottom multi-well microplate 210. Well mask layer 212 may be, for example, about 20-200 μm thick. Microposts layer 214 may be, for example, a sheet of microposts 120 disposed on substrate 122, wherein the size of the sheet substantially corresponds to the footprint of open bottom multi-well microplate 210. In microposts layer 214, microposts 120 are facing toward open bottom multi-well microplate 210. A "Detail A" of FIG. 4 shows a magnified view of a portion of microposts layer 214. In this example, microposts 120 may be about 4 μm in diameter and about 50 μm tall. Backing layer 216 may be, for example, an acrylic backing layer that may be about 0.25-2 mm thick.

Additionally, well mask layer 212 provides a gasket layer to prevent leaking from one vessel 110 to another when micropost layer 214 is pressed against open bottom multi-well microplate 210. However, in some embodiments, well mask layer 212 may be omitted and micropost layer 214 is bonded directly to open bottom multi-well microplate 210. For example, bonding methods such as direct ultrasonic or thermal welding may be used, or perhaps the PDMS itself may serve as a silicone gasket.

FIG. 5 is a top view, a side view, and a cross-sectional view of the small-volume well platform 200 shown in FIG. 4. In this example, the overall footprint of small-volume well platform 200 may be substantially the same as a standard multi-well microplate. For example, small-volume well platform 200 may be about 127.76 mm (5.03 in) long, about 85.48 mm (3.36 in) wide, and about 15.5 mm (0.61 in) thick. The 96 small-volume vessels 110 may be arranged about 9 mm (0.35 in) apart (on center) in both X and Y.

Figures 5A, 5B:
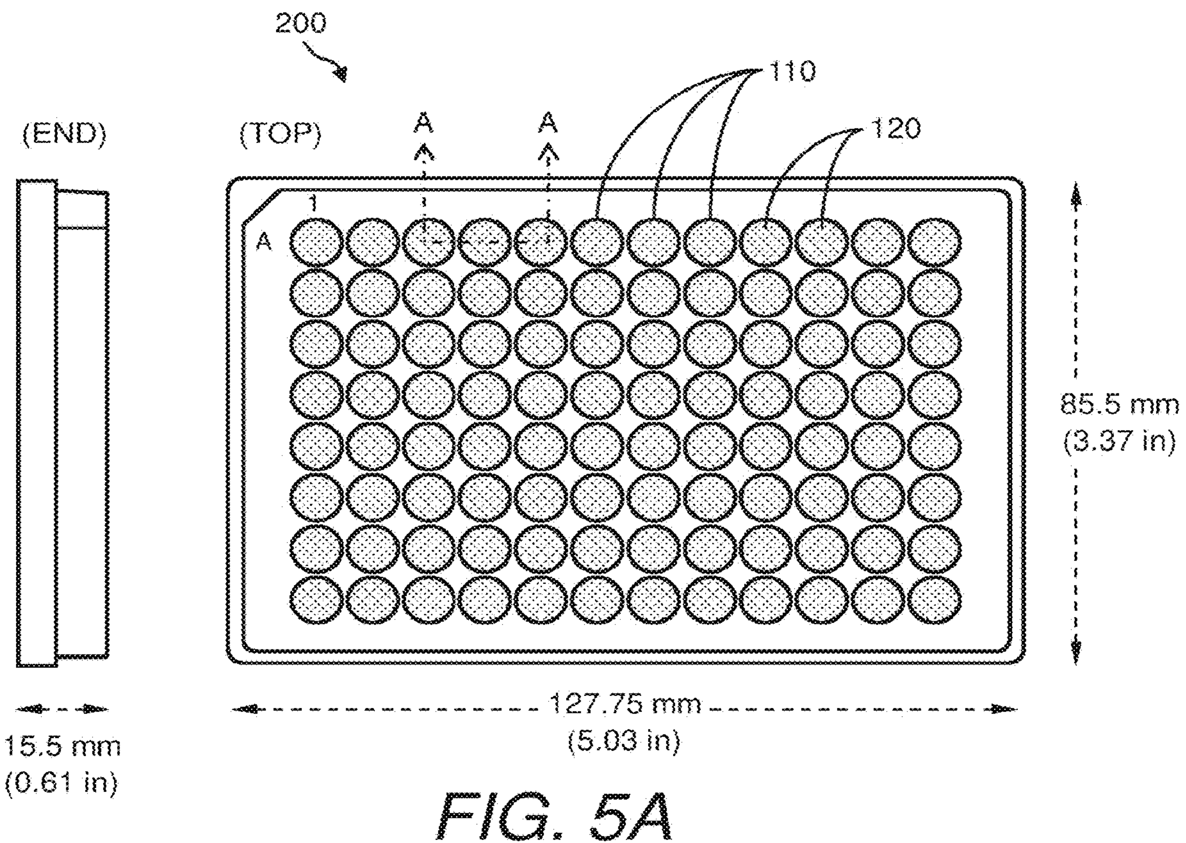
FIG. 5 illustrates a top view, a side view, and a cross-sectional view of the small-volume well platform shown in FIG. 4.

Referring now to the cross-sectional view of small-volume well platform 200 in FIG. 5B, which is taken along line A-A of the top view. The stack of open bottom multi-well microplate 210, well mask layer 212, microposts layer 214, and backing layer 216 may be held together via adhesive on both well mask layer 212 and backing layer 216. In one example, the assembly process of small-volume well platform 200 may be (1) provide open bottom multi-well microplate 210; (2) align and adhere well mask layer 212 against the bottom surface of open bottom multi-well microplate 210, (3) press a sheet of microposts layer 214 against well mask layer 212. In so doing, certain microposts 120 may land against the space outside the openings of well mask layer 212 and may be crushed while other microposts 120 land inside the openings of well mask layer 212 and thus are undamaged and fully functional; and (4) align and adhere backing layer 216 against microposts layer 214. At the completion of this process, the 96 small-volume vessels 110 are formed in small-volume well platform 200 and wherein each small-volume vessel 110 includes a field or array of actuatable surface-attached microposts 120.

Small-volume well platform 200 of microbioreactor system 100 is well suited for use in an automated liquid handler system. For example, when using small-volume well platform 200, liquid delivery mechanism 142 may be a set of robotics-based dispensing pipettes (not shown) and liquid removal mechanism 144 may be a set of robotics-based aspirating pipettes (not shown). In an automated liquid handler system, the operation of microbioreactor system 100 and small-volume well platform 200 may be classified as batch, fed batch, and/or continuous.

Figure 6:
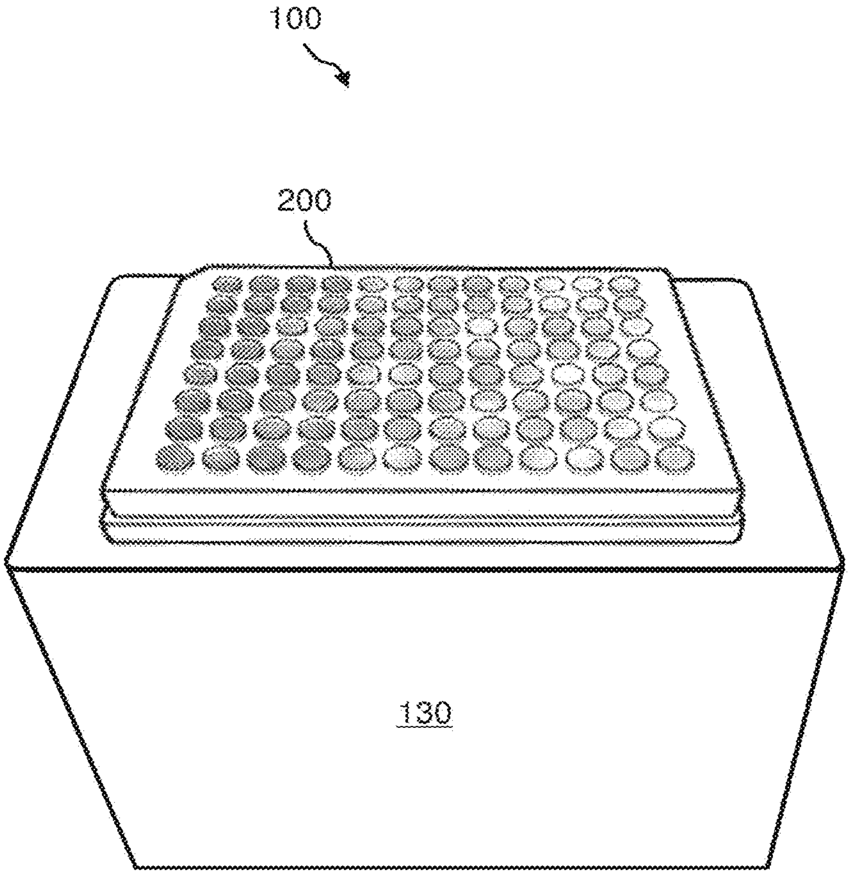
FIG. 6 shows a perspective view of one example instantiation of the microbioreactor system for providing cell culture growth conditions including enhanced oxygenation and nutrients distribution in a small-volume vessel.

FIG. 6 is a perspective view of one example instantiation of the microbioreactor system 100 for providing cell culture growth conditions including enhanced oxygenation and nutrients distribution in a small-volume vessel 110. Each instantiation includes, for example, a small-volume well platform 200 including 96 small-volume vessels 110. Additionally, each instantiation may include, for example, a magnetic actuation mechanism 130 that is customized to the footprint of small-volume well platform 200, such that small-volume well platform 200 may sit atop magnetic actuation mechanism 130. In this way, each of the 96 small-volume vessels 110 is within the actuation force 132 of magnetic actuation mechanism 130.

In one example, actuation force 132 of magnetic actuation mechanism 130 may be a rotating magnetic field expressed in rotations per minute (RPM). In this example, the actuation and/or mixing rate of microposts 120 in each small-volume vessel 110 may correlate to the RPM of magnetic actuation mechanism 130. For example, the RPM of magnetic actuation mechanism 130 may be adjustable up to a few thousand RPMs. The distance of magnetic actuation mechanism 130 from microposts 120 in small-volume well platform 200 may determine the tilt angle $\alpha$ (see FIG. 2B) of microposts 120. However, generally magnetic actuation mechanism 130 may be configured to actuate the magnetically responsive surface-attached microposts 120 in certain beat patterns, such as synchronized beat patterns and/or metachronal beat patterns.

Each instantiation of microbioreactor system 100 shown in FIG. 6 may be suitable for use in, for example, an automated liquid handler or microplate cell feeding system. Additionally, each instantiation of microbioreactor system 100 shown in FIG. 6 may include any other useful components. For example, heating mechanisms, optical detection mechanisms, gas sensors (e.g., O2 sensors), pH sensors, and/or any other sensing mechanisms may be integrated into and/or near the body holding magnetic actuation mechanism 130.

Figure 7A:
FIG. 7A shows a plot indicating the mixing efficiency of actuatable surface-attached microposts in cell culture small-volume vessels.
Figure 7A:
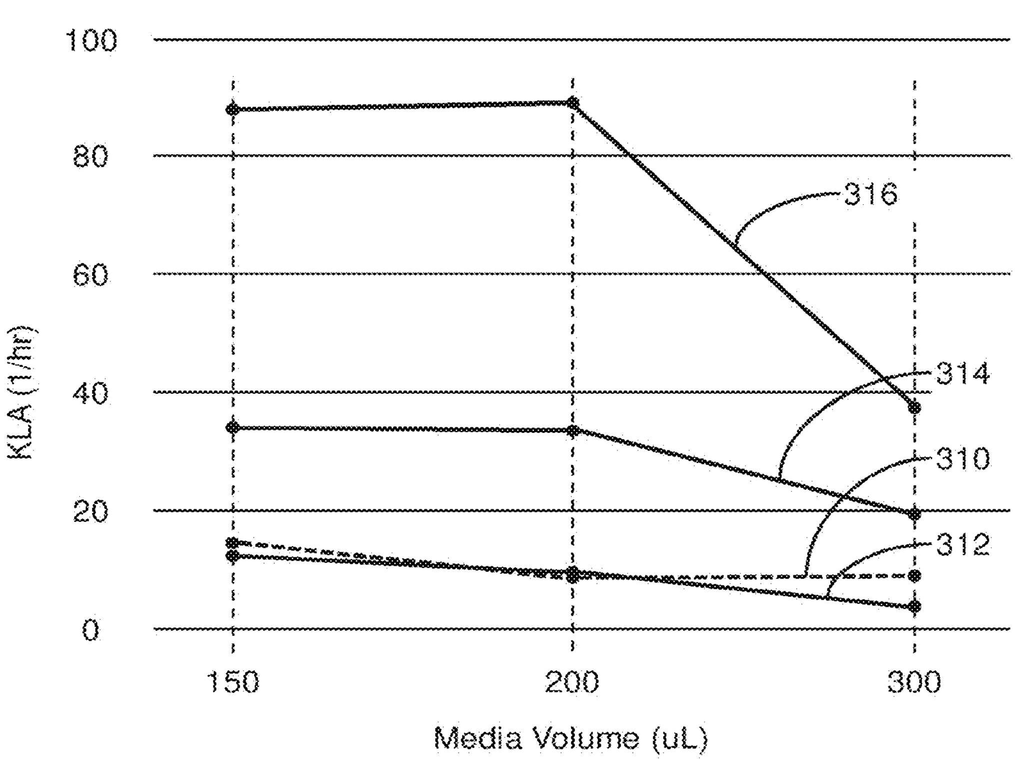
Figure 7B:
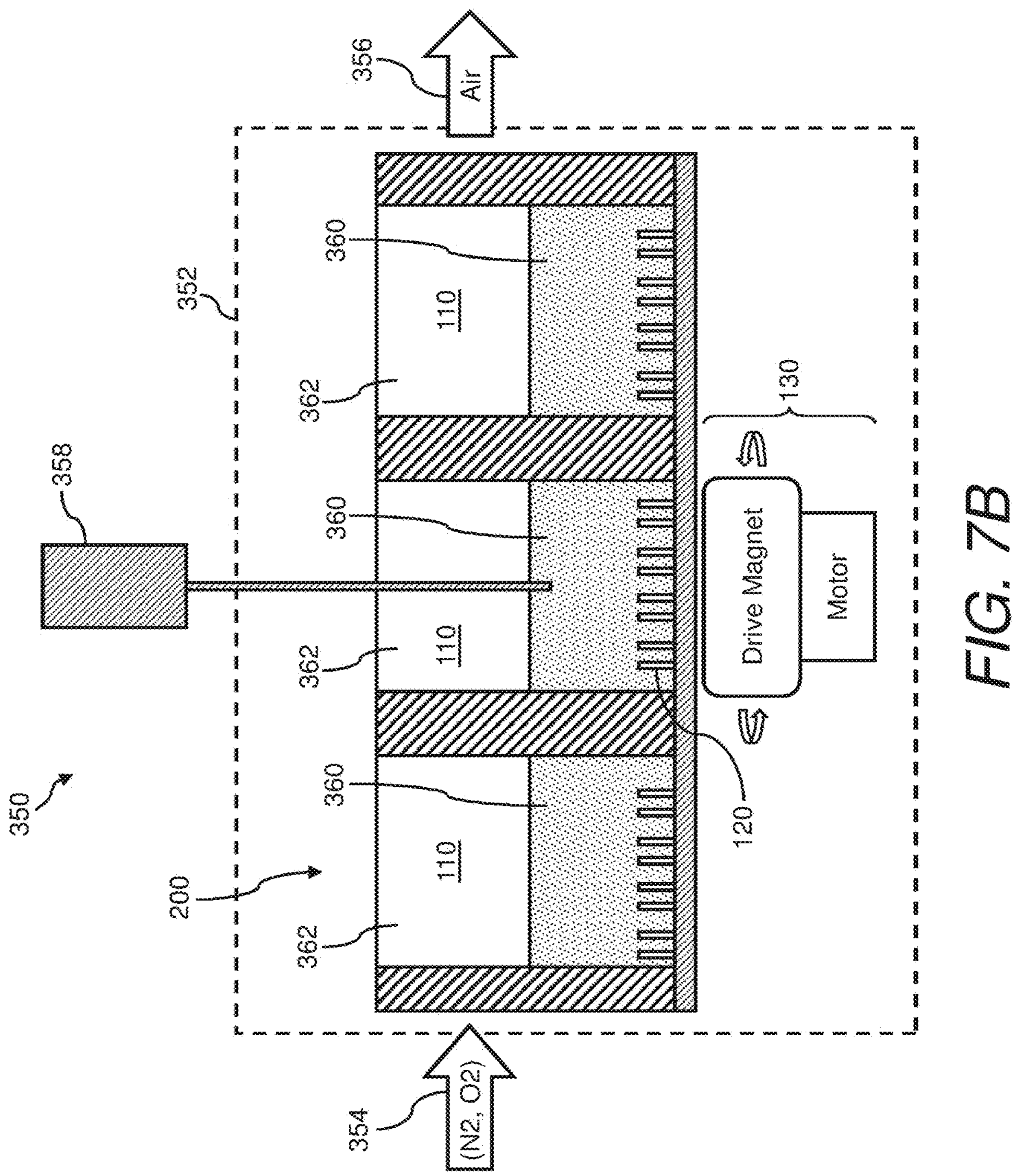
FIG. 7B is a schematic diagram of an example of a kLa evaluation chamber for performing the experiments associated with the plot shown in FIG. 7A.

FIG. 7A shows a plot 300 indicating the mixing efficiency of actuatable surface-attached microposts 120 in cell culture small-volume vessels, such as small-volume vessels 110. FIG. 7B is a schematic diagram of an example of a kLa evaluation chamber 350 for performing the experiments associated with plot 300 shown in FIG. 7A. For example, plot 300 indicates kLa (oxygen transfer coefficient) vs. media volume for various media volumes and various RPMs of magnetic actuation mechanism 130. In this example, (1) the media volumes (e.g., 150 μL, 200 μL, 300 μL) correspond to certain sized small-volume vessels 110, and (2) the RPMs (e.g., 3500, 6500, 9000) correspond to the actuation and/or mixing rate of magnetically responsive surface-attached microposts 120 in each media volume.

In plot 300, a zero RPM curve 310 provides a baseline that indicates kLa with no mixing (e.g., with magnetic actuation mechanism 130 turned off). Next, a 3500 RPM curve 312 indicates substantially no improvement in kLa at media volumes 150 μL, 200 μL, and 300 μL. Next, a 6500 RPM curve 314 indicates a certain improvement in kLa at media volumes 150 μL, 200 μL, and 300 μL. Next, a 9000 RPM curve 316 indicates yet more improvement in kLa at media volumes 150 μL, 200 μL, and 300 μL. Accordingly, plot 300 indicates good mixing efficiency of actuatable surface-attached microposts 120 at 6500 RPM and above in all three media volumes 150 μL, 200 μL, and 300 μL.

kLa evaluation chamber 350 shown in FIG. 7B, kLa evaluation chamber 350 may include, for example, a 96-well small-volume well platform 200 arranged inside a sealed air chamber 352 (e.g., a sealed acrylic chamber). Sealed air chamber 352 has a gas inlet 354 for receiving, for example, nitrogen (N2) and/or oxygen (O2) and a gas outlet 356 for exhausting, for example, air. Each small-volume vessel 110 may be holding a certain amount of liquid 360 and air 362. In this example, liquid 360 is distilled water. A dissolved oxygen probe 358 is inserted into liquid 360 in any one of the small-volume vessels 110. Magnetic actuation mechanism 130 (e.g., rotating magnet driven by a motor) is provided for actuating surface-attached microposts 120 in small-volume vessels 110.

Using kLa evaluation chamber 350, kLa values were determined using a dynamic gassing out method. Generally, the kLa data indicated in plot 300 was collected using distilled water as the liquid. These kLa mixing studies were performed in a "cell-free/biomass free" environment. The 96-well small-volume well platform 200 and magnetic actuation mechanism 130 were placed in the sealed air chamber 352 that has gas inlet 354 and gas outlet 356. Small ports were bored into the top of sealed air chamber 352 to allow real-time measurements via retractable dissolved oxygen probes 358, such as retractable fiber oxygen microprobes (OXR50 Pyroscience) connected to an oxygen sensor (FireStringO2 Pyroscience). Data collected were analyzed using manufacturer provided software (Pyroscience).

Experimental conditions were set prior to placing the 96-well small-volume well platform 200 and magnetic actuation mechanism 130 into sealed air chamber 352 and sealing from the outside environment. The sealed air chamber 352 was then purged of oxygen by flushing with N2 gas until dissolved oxygen concentration was reduced to about zero. Afterward, O2 was slowly re-introduced to the sealed air chamber 352 with the magnetic actuation mechanism 130 either active (3500, 6500, 9000 RPM) or disengaged, and the dissolved oxygen of different well volumes (150, 200, 300 μL) was monitored in real-time until the system returned to steady state. The re-oxygenation rate was determined from the slope of the graph, $\ln(C_{L0}-C_1/C_{L0}-C_s)$ vs. t, and is reported as kLa (1/hr) as shown in plot 300 of FIG. 7A.

FIG. 8 shows a plot 400 indicating the mixing efficiency of traditional small-volume culture wells in response to varying orbital shaking frequency. For example, plot 400 indicates kLa (oxygen transfer coefficient) vs. shaking frequency for various shaking diameters or well diameters. Plot 400 shows a 3 mm shaking diameter curve 410, a 6 mm shaking diameter curve 412, a 25 mm shaking diameter curve 414, 3 mm shaking diameter points 420, 6 mm shaking diameter points 422, and 25 mm shaking diameter points 424. Plot 400 shows a comparison between measured kLa and OTRmax (i.e., 3 mm shaking diameter points 420, 6 mm shaking diameter points 422, and 25 mm shaking diameter points 424) values and calculated values (i.e., 3 mm shaking diameter curve 410, 6 mm shaking diameter curve 412, 25 mm shaking diameter curve 414) for a conventional 96-well microplate for different shaking diameters and shaking frequencies.

In plot 400, the diameters correspond to volume (i.e., the larger diameter the larger volume). At shaking frequency=200 there is substantially no change in kLa at any diameter. However, for larger wells, e.g., 25 mm and up (not shown), there is improvement at about shaking frequency=300 and up. A 96-well microplate that has, for example, 6 mm diameter wells requires shaking frequency=600+ for improved kLa. Therefore, a conclusion can be made that the smaller the well, the faster the required shaking frequency to achieve a high kLa value. In microbioreactor system 100 and small-volume vessel 110, instead of shaking to get oxygen transport and even nutrients distribution, microposts 120 are provided that can be actuated rapidly.

Figure 9:
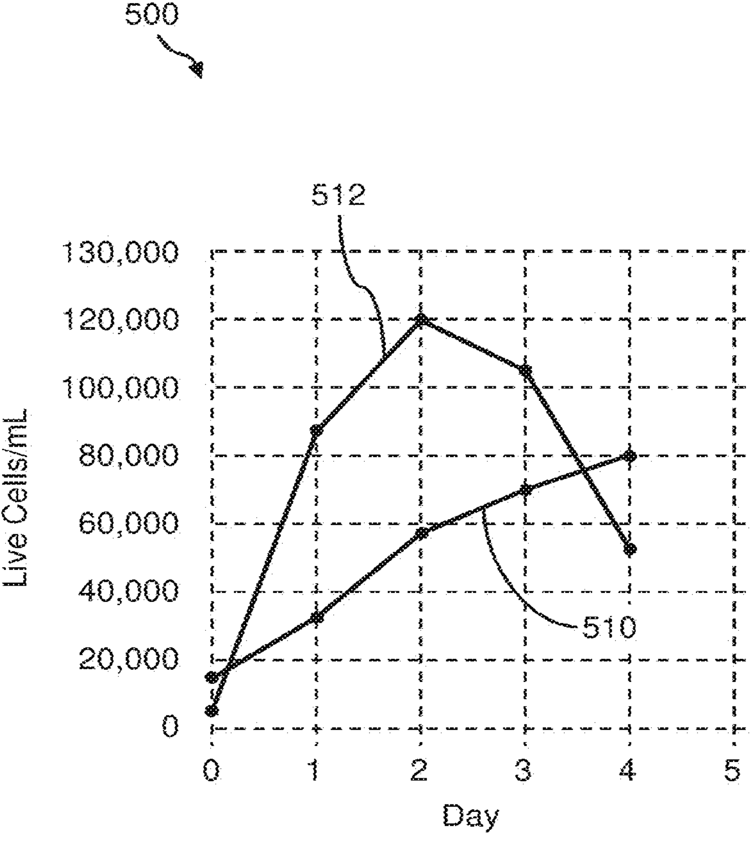
FIG. 9 and FIG. 10 show plots indicating the enhanced proliferation of T-cells and CHO cells, respectively, as a result of the mixing action of microposts.
Figure 10:
Figure 10:
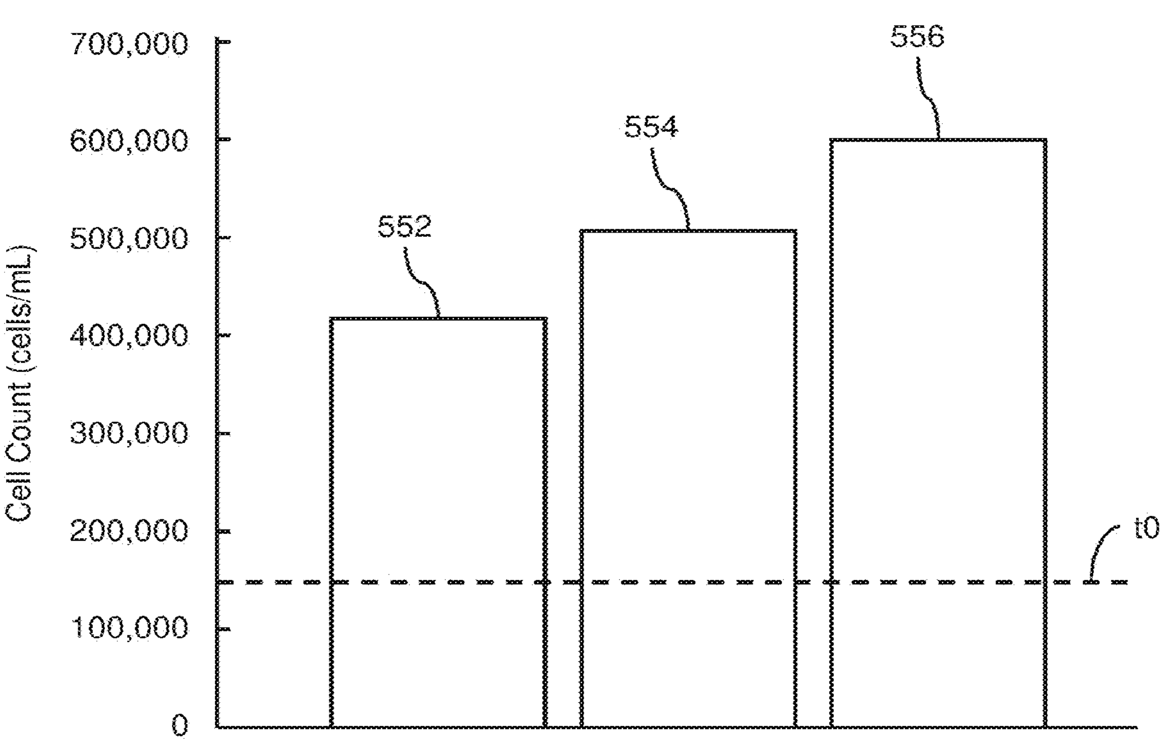

FIG. 9 and FIG. 10 show plots indicating the enhanced proliferation of T-cells and CHO cells, respectively, as a result of the mixing action of microposts 120. For example, a plot 500 shown in FIG. 9 indicates the number of live cells vs. time (e.g., days) with and without the mixing action of microposts 120. An unmixed curve 510 provides a baseline that indicates the number of live cells vs. time with no mixing (e.g., with magnetic actuation mechanism 130 turned off). Next, a mixed curve 512 indicates the number of live cells vs. time with mixing present (e.g., with magnetic actuation mechanism 130 turned on). For day 1 and day 2, mixed curve 512 indicates a significantly greater cell growth rate as compared with unmixed curve 510. Mixed curve 512 then drops off, likely because of the depletion of growth nutrients. To maintain the high growth rate day after day as indicated by mixed curve 512, the growth media must be exchanged more frequently. By contrast, unmixed curve 510 continues growth beyond day 2, likely because the growth nutrients are not yet depleted because of the slower growth rate. Accordingly, plot 500 indicates that the mixing action of microposts 120 promotes cell growth. For plot 500, data was collected using microbioreactor system 100.

Referring still to plot 500 of FIG. 9, donor CD4+ naïve T cells (Astarte Biologics) were cultured in X-VIVO serum free media (Lonza) supplemented with varying concentrations of recombinant human IL-2, IL-7, and IL-15. T-cells were activated with the anti-CD3/anti-CD28 Dynabeads (ThermoScientific) at a ratio of 1:1. Cells were seeded in the 96-well small-volume well platform 200 at a concentration of 166,667 cells/mL per well with a volume of 300 μL. The drive system (e.g., magnetic actuation mechanism 130) was set to duty-cycle (5 min ON, 55 min. OFF) at 4000 rpm. The drive system was then placed inside a cell culture incubator at 37° C. with a humidified atmosphere at 5% $CO_2$. Cell concentration (cells/mL) was determined by direct count with a hemocytometer for the evaluation of growth under each culture condition (Mix-No Mix).

Plot 550 shown in FIG. 10 shows an example of enhanced growth of growing CHO cells using the microbioreactor system 100. Generally, plot 550 is a bar graph that shows enhanced growth while mixing with microposts 120 compared to wells with static posts and standard growth plate (non-shaking) conditions after 72 hours. Plot 550 indicates, for example, a control culture 552, microposts without mixing culture 554, and microposts with mixing culture 556. Plot 550 also shows a line t0 indicating the cell seeding density at time=0. Control culture 552 is a 96-well standard (t=72 hrs), microposts without mixing culture 554 is a culture with microposts 120 not actuated (t=72 hrs), and microposts with mixing culture 556 is a culture with microposts 120 actuated (t=72 hrs).

CHO-S cells (Gibco) were cultured in Freestyle CHO expression medium (Gibco) supplemented with 8 mM L-glutamine (Gibco), 0.1% Kolliphor P188 (Sigma), and 0.5× Pen/Strep (Gibco). Cells (passage 3-7) were transferred from active culture in a 125-mL shake flask and seeded in the 96-well small-volume well platform 200 at a concentration of 150,000 cells/mL per well with a volume of 300 μL. The drive system (e.g., magnetic actuation mechanism 130) was set to duty-cycle (10 min ON, 50 min OFF) at 6000 rpm and placed inside a cell culture incubator at 37° C. with a humidified atmosphere at 8% $CO_2$. Total protein values for each culture condition at the end of a 72-h culture period were determined by Bradford protein assay (Pierce) following complete cell lysis. The resulting protein values were reported as cell concentration (cells/mL) after comparison to a standard protein curve obtained from known CHO-S cell counts.

Figure 11:
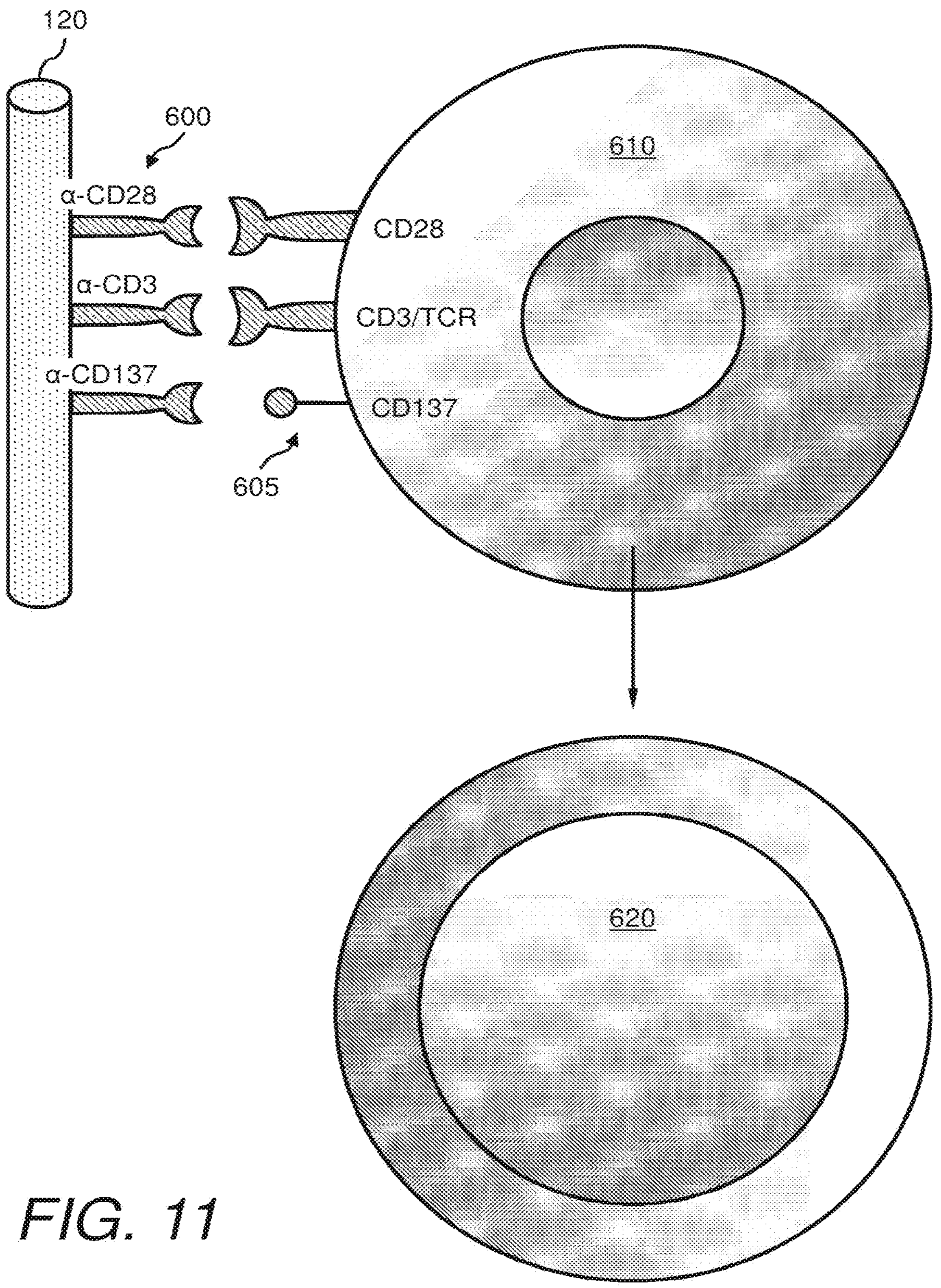
FIG. 11 illustrates a schematic diagram of an example of a micropost that is functionalized for producing activated T-cells in a small-volume vessel of the microbioreactor system.

FIG. 11 is a schematic representation of a micropost 120 that is functionalized for producing activated T-cells in a small-volume vessel 110 of the microbioreactor system 100. T-cell activation means the change in morphology and behavior of a T-cell in response to interacting with certain signaling proteins. For example, FIG. 11 shows an example of a micropost 120 that is functionalized with activation signals 600. The functionalized micropost 120 mimics antigen presenting cells (APCs) inside the body that allow normal T-cells to be activated and turn them into activated T-cells. In this example, activation signals 600 on functionalized micropost 120 may come into contact with T-cell receptors 605 of a normal T-cell 610 and produce an activated T-cell 620.

In one example, normal T-cell 610 may be an Ag-specific T-cell 610. Micropost 120 may be functionalized with an α-CD28 activation signal 600 for contacting a CD28 T-cell receptor 605, an α-CD3 activation signal 600 for contacting a CD3/TCR T-cell receptor 605, and an α-CD137 activation signal 600 for contacting a CD137 T-cell receptor 605. In this example, an activated Ag-specific T-cell 620 may be produced.

The actuatable surface-attached microposts 120 in small-volume vessels 110 of microbioreactor system 100 may be functionalized microposts 120 as shown and described in FIG. 11. Accordingly, in microbioreactor system 100, these functionalized microposts 120 may be used in small-volume vessels 110 to activate and expand T-cells in a cell culture application.

In conventional cell culture, beads functionalized with the activation signals may be used to activate and expand T-cells. A drawback of this process is that the beads are often mixed with the activated T-cells that are produced and throw off the count of the activated T-cells. Therefore, a benefit of the microbioreactor system 100 in this embodiment is that it uses functionalized microposts 120, not functionalized beads, to activate T-cells in small-volume vessels 110 and wherein the activated T-cells may be produced in a manner that can be counted accurately because beads that can be mistakenly counted as cells are not present. Another benefit of the microbioreactor system 100 that uses functionalized microposts 120 instead of functionalized beads is that it eliminates any downstream processes of separating beads from cells.

Figure 12:
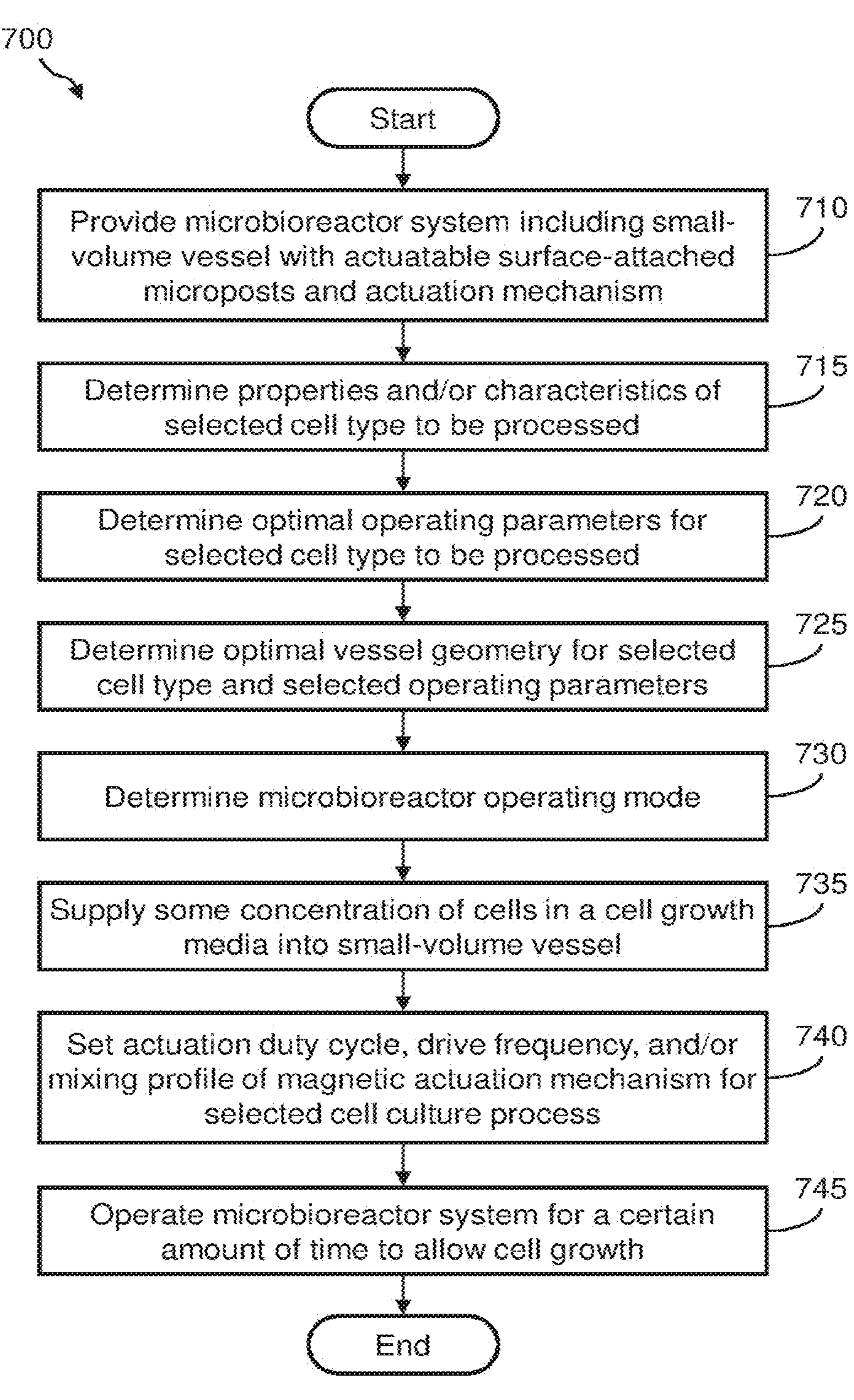
FIG. 12 illustrates a flow diagram of an example of a method of using the microbioreactor system for providing cell culture growth conditions including enhanced oxygenation and nutrients distribution in a small-volume vessel.

FIG. 12 is a flow diagram of an example of a method 700 of using the microbioreactor system 100 for providing cell culture growth conditions including enhanced oxygenation and nutrients distribution (or homogenization) in a small-volume vessel. Method 700 may include, but is not limited to, the following steps.

At a step 710, microbioreactor system 100 including small-volume vessel 110 with actuatable surface-attached microposts 120 and actuation mechanism 130 is provided. For example, microbioreactor system 100 is provided that may include one or more small-volume vessels 110 and magnetic actuation mechanism 130 as described, for example, in FIG. 1 through FIG. 11. In one example, microbioreactor system 100 may be the system shown in FIG. 6, which is small-volume well platform 200 sitting atop magnetic actuation mechanism 130. The actuatable surface-attached microposts 120 may be functionalized with, for example, activation signals for converting standard T-cells in a growth media into activated T-cells.

At a step 715, the properties and/or characteristics of the selected cell type to be processed are determined. For example, a T-cell may have different properties and/or characteristics than a CHO cell. In method 700, one must balance the tolerance of the cells to mechanical abuse or damage vs. the required nutrients distribution. For example, with respect to the mechanical tolerance, different cell types may tolerate the mixing action of actuatable surface-attached microposts 120 differently. That is, one cell type may tolerate a certain actuation duty cycle and/or RPM of magnetic actuation mechanism 130 without damage to the cell, while another cell type may tolerate a different actuation duty cycle and/or RPM of magnetic actuation mechanism 130 without damage to the cell. With respect to nutrient distribution, different cell types may consume nutrients at different rates and therefore require different mixing rates and/or nutrients delivery rates. These and other characteristics described herein may be determined experimentally by one of skill in the art in view of this specification.

At a step 720, the optimal operating parameters for the selected cell type to be processed are determined. For example, optimal operating parameters, such as, but not limited to, actuation duty cycle, actuation drive frequency (e.g., RPM), actuation mixing profile are determined for the selected cell type; all per the control of magnetic actuation mechanism 130. An example of the actuation duty cycle may be a one sixth duty cycle, such as 10 minutes on, then 50 minutes off. An example of the actuation drive frequency may be 4000 RPM. An example of the actuation mixing profile may be a rotating magnetic field, any synchronized beat patterns, and/or any metachronal beat patterns.

Other process variables and/or parameters may include, but are not limited to, feeding time, feeding amount, concentrations of critical factors (e.g., sugar), pH level, temperature, signaling factors (e.g., varying the amounts and/or concentrations of the activation signals on microposts 120), adding other stimuli for promoting T-cell growth, varying the volume of liquid in the selected well size, mixing rate, density of microposts 120, varying the surface area to volume ratio of small-volume vessel 110, and the like.

At a step 725, the optimal vessel geometry for the selected cell type and selected operating parameters is determined. For example, the optimal headspace in small-volume vessel 110 above the actuatable surface-attached microposts 120 for the selected cell type and selected operating parameters is determined.

At a step 730, the operating mode of microbioreactor system 100 including small-volume vessel 110 with actuatable surface-attached microposts 120 is determined. For example, batch, fed-batch, and/or continuous vs. profusion operating mode is determined.

At a step 735, some concentration of cells in a cell growth media is supplied into small-volume vessel 110. For example, some concentration of cells (e.g., suspension cells 146) in a cell growth media (e.g., growth media 140) is supplied into small-volume vessel 110 using liquid delivery mechanism 142 (e.g., manual and/or automated pipetting).

At a step 740, the actuation duty cycle, actuation drive frequency (e.g., RPM), and/or actuation mixing profile of magnetic actuation mechanism 130 are set for the selected cell culture process.

At a step 745, microbioreactor system 100 is operated for a certain amount of time to allow cell growth. For example, microbioreactor system 100 is operated for 5 hours with a one sixth actuation duty cycle (e.g., 10 minutes on, 50 minutes off) and a rotating magnetic field at 4000 RPM.

Figure 13:
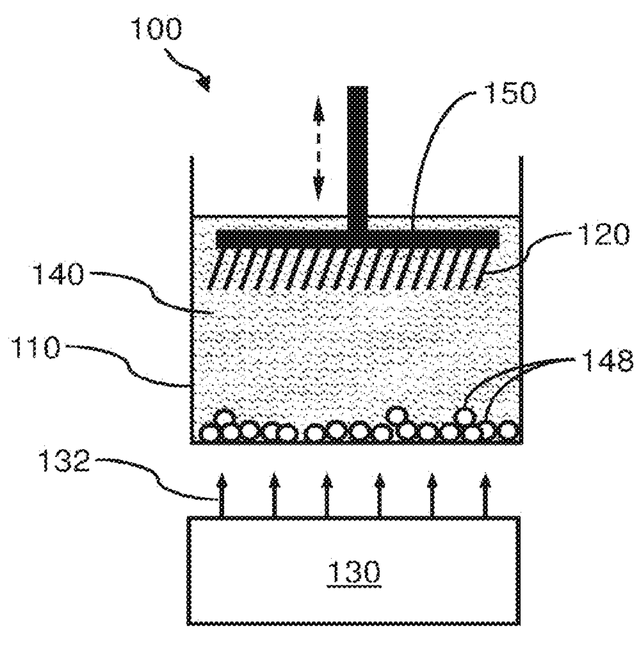
FIG. 13 illustrates a side view of an example of a configuration of the small-volume vessel of the microbioreactor system that may be utilized for an adherent cell culture.

FIG. 13 is a side view of an example of a configuration of small-volume vessel 110 of microbioreactor system 100 that may be utilized for an adherent cell culture. It should be noted that although this configuration is particularly useful for adherent cells, it may also be useful for suspended cells or mixtures of adherent and suspended cells.

In this example, microbioreactor system 100 includes a topside microposts platform 150 in relation to the top of small-volume vessel 110. Topside microposts platform 150 holds a field or array of the actuatable surface-attached microposts 120 that are directed toward and into growth media 140. Topside microposts platform 150 may be fixed or retractable with respect to small-volume vessel 110. In this example, a quantity of adherent cells 148 may be settled at the bottom of small-volume vessel 110. In this example, the actuatable surface-attached microposts 120 may be driven from either above or below via magnetic actuation mechanism 130.

An example of a mechanism that may be used to form topside microposts platform 150 is the CellCrown™ inserts (available from Sigma-Aldrich Corp., St. Louis, MO), which are structures that are normally used to hold optical sensing components. CellCrown™ inserts may be, for example, in the form of plastic 96-well plate inserts, 48-well plate inserts, 8-well strips, and the like. In one example, topside microposts platform 150 may be the CellCrown 96 insert, which is a plastic cell culture insert for standard 96 well plates, and wherein microposts 120 may be installed on the CellCrown 96 insert.

The configuration of small-volume vessel 110 shown in FIG. 13 positions the microposts 120 out of the way of the adherent cells 148. Accordingly, the microposts 120 of topside microposts platform 150 provide a way to create mixing action and stir up some amount of adherent cells 148 to be processed while at the same time avoiding interference of the adherent cells 148 with the microposts 120.

Figure 14:
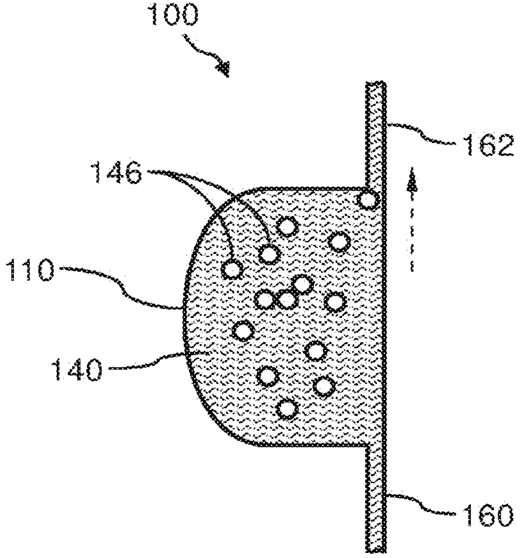
FIG. 14 illustrates a side view of an example of a configuration of the small-volume vessel of the microbioreactor system that may utilized in a cell culture having a constant flow of growth media.

FIG. 14 is a side view of an example of a configuration of small-volume vessel 110 of microbioreactor system 100 that may be utilized in a cell culture having a constant flow of growth media. In this example, small-volume vessel 110 may be a small-volume vessel or chamber that has a field or array of actuatable surface-attached microposts (not shown). Small-volume vessel 110 includes an inlet channel 160 and an outlet channel 162.

In this configuration, small-volume vessel 110 may be filled with growth media 140 that include suspension cells 146 to be processed. A constant flow of growth media 140 is provided via inlet channel 160 and outlet channel 162. For example, in a constant flow cell culture application, a constant flow of growth media 140 is provided, while at the same time it is desired to retain the suspension cells 146 to be processed, i.e., to not allow suspension cells 146 to exit small-volume vessel 110 in the flow. Accordingly, in this example, inlet channel 160 and outlet channel 162 are sized smaller than the expected diameter of suspension cells 146. In this way, suspension cells 146 may be physically blocked from exiting small-volume vessel 110. That is, suspension cells 146 may be too large to flow through outlet channel 162 and out of small-volume vessel 110. Filters may be provided in inlet or outlet channels, e.g., for cell retention purposes.

To support cell culture growth conditions, in one example, a vapor permeable lid may be provided on small-volume vessel 110. Via the vapor permeable lid, oxygen may enter small-volume vessel 110 and provide adequate oxygenation. In another example, growth media 140 may be oxygenated in advance of entering small-volume vessel 110. Additionally, substrate 122 that supports the surface-attached microposts 120 (see FIG. 2A and FIG. 2B) is itself formed of a vapor permeable material (e.g., PDMS) and may allow a source of oxygen to small-volume vessel 110.

Figure 15:
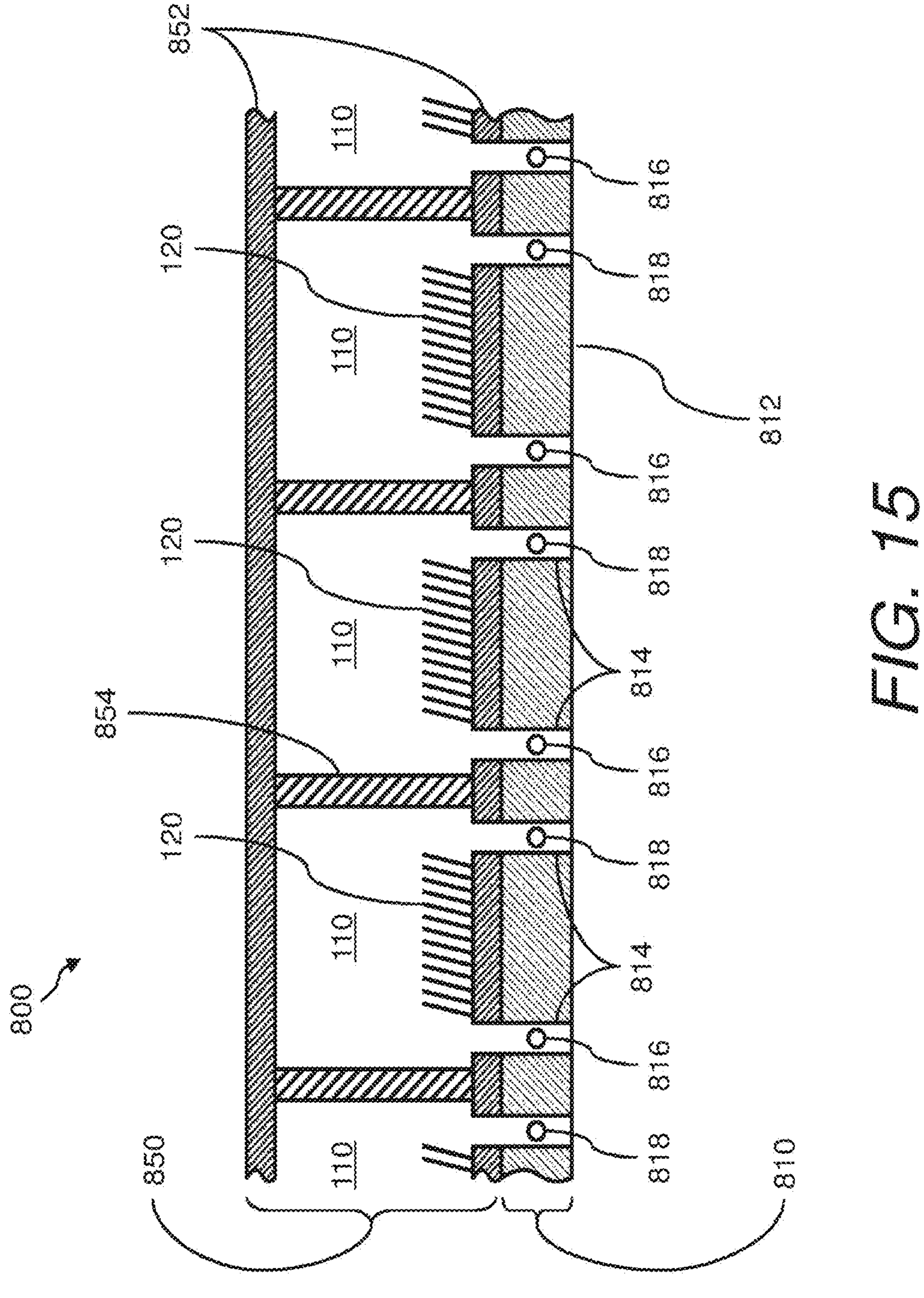
FIG. 15 and FIG. 16 illustrate a cross-sectional view and a top view, respectively, of an example of a wafer-level microbioreactor structure, which may be suitable for use in the microbioreactor system.
Figure 16:
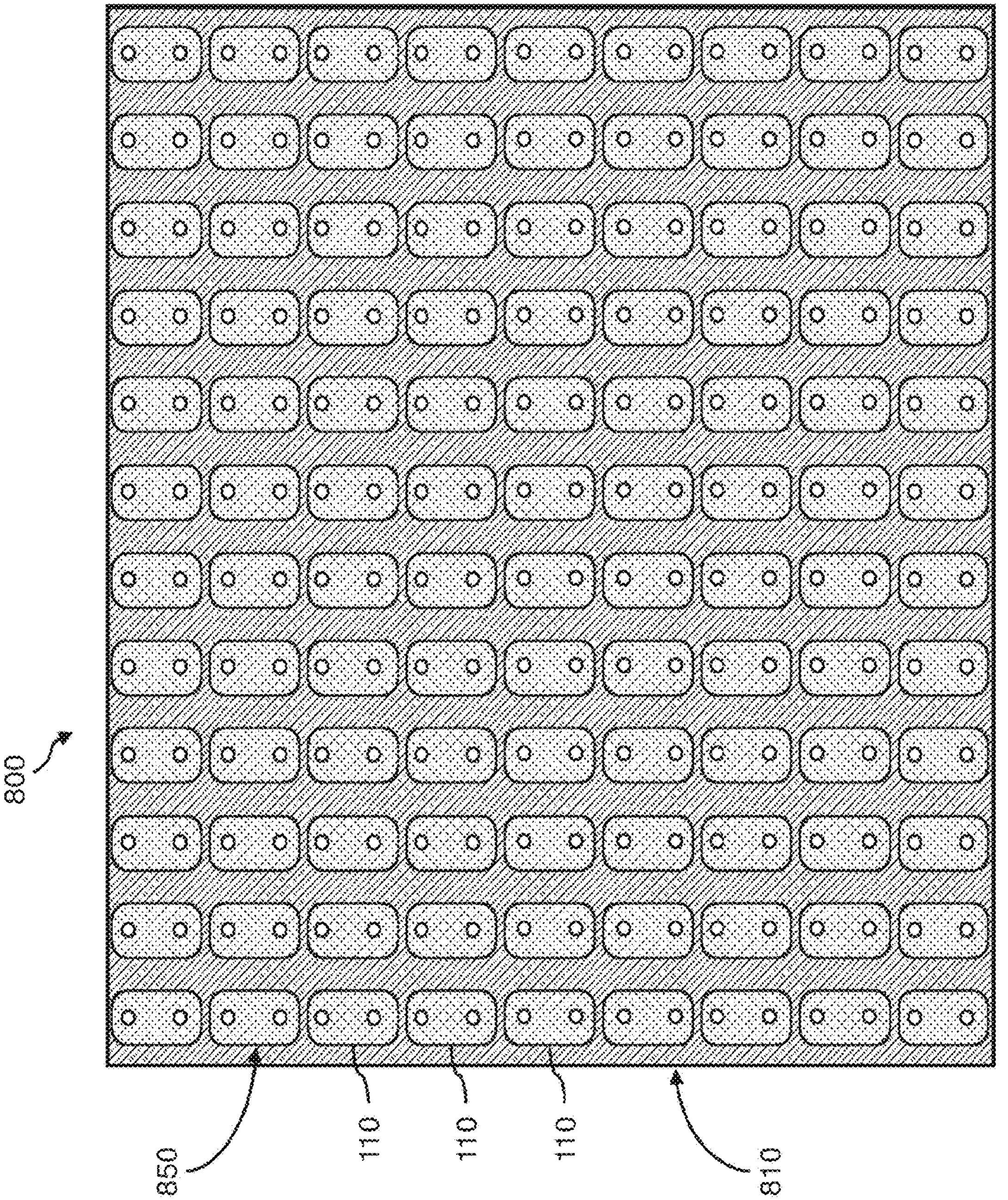

FIG. 15 and FIG. 16 show a cross-sectional view and a top view, respectively, of an example of a wafer-level microbioreactor structure 800, which may be suitable for use in the microbioreactor system 100. Wafer-level microbioreactor structure 800 includes a manifold portion 810 that supports a vessel portion 850 and wherein wafer-level microbioreactor structure 800 is designed for the mass production and/or operation of small-volume vessels 110.

Manifold portion 810 may include, for example, a manifold substrate 812 that includes a plurality of through-hole vias 814 (hereafter called vias 814). Manifold substrate 812 may be, for example, a silicon substrate (e.g., silicon wafer). A plurality of inlet channels 816 and outlet channels 818 are running through manifold substrate 812 to respective vias 814. For example, while vias 814 are substantially perpendicular to the plane of manifold substrate 812, inlet channels 816 and outlet channels 818 run substantially parallel to the plane of manifold substrate 812 such that they may intersect with vias 814.

Vessel portion 850 of wafer-level microbioreactor structure 800 is then built atop manifold substrate 812 of manifold portion 810. In one example, vessel portion 850 atop manifold substrate 812 includes a vapor permeable layer 852, then a field or array of surface-attached microposts 120, then a mask layer 854, and then another vapor permeable layer 852. In another example, wafer-level microbioreactor structure 800 may include the top vapor permeable layer 852 only. In this example, vias 814 of manifold substrate 812 extend through the near vapor permeable layer 852 and the layer of microposts 120 to provide at least one liquid input port and one liquid output port at each small-volume vessel 110.

Openings in mask layer 854 define an arrangement of small-volume vessels 110, as shown for example in FIG. 16. Accordingly, small-volume vessels 110 of wafer-level microbioreactor structure 800 may be closed vessels rather than open vessels as described in small-volume well platform 200. In wafer-level microbioreactor structure 800, the well-volume capacity of each of the small-volume vessels 110 may be, for example, from about a few microliters (μL) to about a few milliliters (mL). In one example, wafer-level microbioreactor structure 800 may be formed according to the process described with reference to U.S. patent application Ser. No. 62/522,536, entitled "Modular Active Surface Devices for Microfluidic Systems and Methods of Making Same," filed on Jun. 20, 2017. For example, the '536 patent application describes an active surface layer mounted atop an active surface substrate, a mask mounted atop the active surface layer wherein the mask defines the area, height, and volume of the reaction chamber, and a substrate mounted atop the mask wherein the substrate provides the facing surface to the active surface layer. The '536 patent application describes a large-scale manufacturing method, which is a method of mass producing the modular active surface devices.

In one example, manifold portion 810 of wafer-level microbioreactor structure 800 may be configured such that one inlet channel 816 and one outlet channel 818 are paired to service one small-volume vessel 110. Accordingly, in manifold portion 810 of wafer-level microbioreactor structure 800, multiple inlet channel 816/outlet channel 818 pairs are provided to service multiple small-volume vessels 110, respectively. Additionally, manifold portion 810 may be configured for different levels of control of small-volume vessels 110. In one example, manifold portion 810 may be configured for mass control of small-volume vessels 110. For example, using a certain configuration of inlet channels 816 and outlet channels 818, manifold portion 810 may be configured such that liquid (e.g., growth media 140) may be supplied to all small-volume vessels 110 in common and liquid may be recovered from all small-volume vessels 110 in common.

In another example, manifold portion 810 may be configured for individual control of small-volume vessels 110. For example, using a certain configuration of inlet channels 816 and outlet channels 818, manifold portion 810 may be configured such that liquid (e.g., growth media 140) may be supplied to each small-volume vessel 110 individually and liquid may be recovered from each small-volume vessel 110 individually.

In yet another example, manifold portion 810 may be configured for multiplex control of small-volume vessels 110. For example, using a certain configuration of inlet channels 816 and outlet channels 818, manifold portion 810 may be configured such that liquid (e.g., growth media 140) may be supplied to groups of small-volume vessels 110 in common and liquid may be recovered from groups of small-volume vessels 110 in common. In one example, manifold portion 810 may be configured for 8-multiplex control of small-volume vessels 110. Accordingly, the plurality of small-volume vessels 110 of wafer-level microbioreactor structure 800 may be configured in groups of eight. In this example, manifold portion 810 may be configured such that liquid (e.g., growth media 140) may be supplied to each of the 8 small-volume vessels 110 in the group in common and liquid may be recovered from each of the 8 small-volume vessels 110 in the group in common, and wherein each group of 8 small-volume vessels 110 may be controlled individually.

If, for example, the top view of wafer-level microbioreactor structure 800 shown in FIG. 16 represents a portion of a wafer, wafer-level microbioreactor structure 800 may be diced depending on the operating configuration. In one example, if manifold portion 810 is configured for mass control of small-volume vessels 110 in microbioreactor system 100, then wafer-level microbioreactor structure 800 may be diced in a manner to include large numbers of small-volume vessels 110. In another example, if manifold portion 810 is configured for individual control of small-volume vessels 110 in microbioreactor system 100, then wafer-level microbioreactor structure 800 may be diced into individual small-volume vessels 110. In yet another example, if manifold portion 810 is configured for multiplex control of small-volume vessels 110 in microbioreactor system 100, then wafer-level microbioreactor structure 800 may be diced in a manner to include certain groups of small-volume vessels 110 (e.g., for 8-multiplex control, one die is 8 small-volume vessels 110). Various other useful components may be integrated into wafer-level microbioreactor structure 800, such as, but not limited to, heating mechanisms, optical detection mechanisms, gas sensors (e.g., O2 sensors), pH sensors, and/or any other sensing mechanisms.

In, for example, batch operating mode of wafer-level microbioreactor structure 800, all small-volume vessels 110 are fed-from a common cell growth media reservoir and waste media exits to a common waste reservoir. Then, cells are grown inside the small-volume vessels 110 for some period of time with mixing occurring at some duty cycle to promote growth, then while retaining cells, small-volume vessels 110 are flushed with fresh growth media while waste media exits. This is, for example, a mix, wait, pump, mix, wait, pump, sequence at some frequency.

In, for example, fed-batch or continuous operating mode of wafer-level microbioreactor structure 800, cell growth media is continuously added to small-volume vessels 110 while at the same time cells are continuously removed from small-volume vessels 110.

In summary and referring now again to FIG. 1 through FIG. 16, the microbioreactor system 100 and method 700 provide a field of actuatable surface-attached microposts 120 for maintaining cell culture growth conditions in a small-volume vessel 110. For example, the well-volume capacity of small-volume vessel 110 may be from about a few microliters (μL) to about a few hundred milliliters (mL). Examples of small-volume vessel 110 may include, but are not limited to, a small-volume flask (e.g., 125 mL shake flask) and/or the individual wells of a standard size multi-well microplate (e.g., standard size 96-well, 48-well, 24-well, 16-well, 12-well, 8-well, 6-well, 4-well microplates, etc.).

Microbioreactor system 100 and method 700 provide a field of actuatable surface-attached microposts 120 for maintaining cell culture growth conditions including, but not limited to, enhanced oxygenation and nutrients distribution (or homogenization) in a small-volume vessel 110.

Microbioreactor system 100 and method 700 provide a field of actuatable surface-attached microposts 120 for maintaining cell culture growth conditions in a small-volume vessel 110 by the mixing action of the microposts 120 and wherein the mixing efficiency of the microposts 120 may be quantified by measuring the oxygen transfer coefficient (kLa) of the cell culture media.

Microbioreactor system 100 and method 700 provide a field of actuatable surface-attached microposts 120 for maintaining cell culture growth conditions in a small-volume vessel 110 and wherein the surface-attached microposts 120 are functionalized with, for example, activation signals for converting standard T-cells in a growth media into activated T-cells. The mixing action of the surface-attached microposts 120 substantially ensures contact between the functionalized microposts 120 and the standard T-cells to be converted into activated T-cells. Using the functionalized microposts 120, activated T-cells may be produced in small-volume vessels 110 in a manner that can be counted accurately in the absence of beads.

The surface-attached microposts 120 may be functionalized with multiple signals for interacting with multiple receptors of the cultured cells. In some cases, the array of wells comprises two or more sets of wells in which each set has microposts functionalized with different molecules or molecule types. In some cases, the microposts within a well include sets of microposts that are functionalized with different molecules or molecule types.

The operation of microbioreactor system 100 and method 700 may be classified as batch, fed-batch, and/or continuous. Microbioreactor system 100 and method 700 provide a low-cost alternative for performing cell culture as compared with standard large-scale bioreactors.

The foregoing subject matter has been described in some detail by way of illustration and example for purposes of clarity of understanding. It will be understood by those skilled in the art that certain changes and modifications can be practiced within the scope of the appended claims.

We claim:

1. A method of maintaining cell culture growth conditions within a small-volume bioreactor, the method comprising:

(a) placing cell culture media in wells of a small-volume well layer of the small-volume bioreactor comprising an array of wells, each well having a top opening and a bottom opening;

(b) placing the cell culture media in contact with an active surface layer of the small-volume bioreactor having an array of actuable surface-attached microposts, wherein the microposts extend into the bottom openings of the array of wells of the well layer;

(c) actuating movement of the surface-attached microposts to create a mixing action whereby the mixing action maintains cell culture growth conditions within the small-volume bioreactor; and (d) measuring an oxygen transfer coefficient (kLa) of the cell culture media to quantify a mixing efficiency of the surface-attached microposts.

2. The method of claim 1, wherein the surface-attached micropost array comprises a magnetically-responsive material.

3. The method of claim 2, wherein the magnetically-responsive material comprises a paramagnetic material, a ferromagnetic material, a ferrimagnetic material, or a metamagnetic material.

4. The method of claim 1, wherein the microposts are functionalized with molecules that interact with cells in the culture to produce a biological effect in the cells.

5. The method of claim 4, wherein the functionalized molecules convert standard T-cells in a growth media to activated T-cells.

6. The method of claim 1, further comprising generating an actuation force in proximity to the active surface layer to actuate the movement of the surface attached microposts, thereby compelling the active surface layer to create the mixing action whereby the mixing action maintains cell culture growth conditions within the wells.

7. The method of claim 1, further comprising generating an actuation force in proximity to the array of actuatable surface-attached microposts to compel the microposts to create the mixing action, whereby the mixing action maintains cell culture growth conditions within the small-volume bioreactor.

8. The method of claim 1, wherein the cell culture growth conditions comprise at least one of enhanced oxygenation and/or nutrient distribution for a selected cell type.

9. The method of claim 1, comprising selecting one or more operating parameters, the operating parameters comprising at least one of actuation duty cycle, actuation drive frequency, and/or actuation mixing profile.

10. The method of claim 1, wherein the cell culture media comprises a concentration of cells.

11. The method of claim 1, wherein the actuating is carried out for an amount of time to allow for cell growth.

12. The method of claim 1, wherein the wells have a volume capacity in the range of from about 0.05 mL to about 100 mL.

13. The method of claim 1, further comprising providing a mask layer between the well layer and the active surface layer.

14. The method of claim 1, wherein the actuating movement is provided by a magnetic actuation mechanism.

* * * * *